US011332513B2

(12) United States Patent
Wu et al.

(10) Patent No.: US 11,332,513 B2
(45) Date of Patent: May 17, 2022

(54) CHIMERIC ANTIGEN RECEPTORS HAVING GITR INTRACELLULAR DOMAIN AS CO-STIMULATORY DOMAIN

(71) Applicants: ProMab Biotechnologies, Inc., Richmond, CA (US); Forevertek Biotechnology Co., Ltd, Hunan (CN); The General Hospital Corporation, Boston, MA (US)

(72) Inventors: Lijun Wu, Albany, CA (US); Marcela V. Maus, Lexington, MA (US); Vita Golubovskaya, Richmond, CA (US)

(73) Assignees: ProMab Biotechnologies, Inc., Richmond, CA (US); Forevertek Biotechnology Co., Ltd, Changsha (CN); The General Hospital Corporation, Boston, MA (US)

( * ) Notice: Subject to any disclaimer, the term of this patent is extended or adjusted under 35 U.S.C. 154(b) by 425 days.

(21) Appl. No.: 16/283,530

(22) Filed: Feb. 22, 2019

(65) Prior Publication Data
US 2019/0177398 A1    Jun. 13, 2019

Related U.S. Application Data

(63) Continuation of application No. PCT/US2017/049385, filed on Aug. 30, 2017.

(60) Provisional application No. 62/381,418, filed on Aug. 30, 2016.

(51) Int. Cl.
C07K 16/28     (2006.01)
C07K 14/705    (2006.01)
C12N 15/62     (2006.01)
C07K 14/71     (2006.01)
C07K 14/725    (2006.01)
C07K 14/47     (2006.01)
C12N 15/85     (2006.01)

(52) U.S. Cl.
CPC .... C07K 14/70578 (2013.01); C07K 14/4748 (2013.01); C07K 14/7051 (2013.01); C07K 14/70517 (2013.01); C07K 14/70521 (2013.01); C07K 14/70596 (2013.01); C07K 14/71 (2013.01); C07K 16/283 (2013.01); C12N 15/62 (2013.01); C12N 15/85 (2013.01); C07K 16/2863 (2013.01); C07K 2317/51 (2013.01); C07K 2317/515 (2013.01); C07K 2317/52 (2013.01); C07K 2317/622 (2013.01); C07K 2319/02 (2013.01); C07K 2319/03 (2013.01)

(58) Field of Classification Search
CPC .......... C07K 14/70578; C07K 14/4748; C07K 14/7051; C07K 14/70517; C07K 14/70521; C07K 14/70596; C07K 14/71; C07K 16/283; C07K 16/2863; C07K 2317/51; C07K 2317/515; C07K 2317/52; C07K 2317/622; C07K 2319/02; C07K 2319/03; C12N 15/62; C12N 15/85
See application file for complete search history.

(56) References Cited

U.S. PATENT DOCUMENTS

2014/0242701 A1   8/2014  Shiku et al.
2014/0322275 A1  10/2014  Brogdon et al.
2016/0185862 A1   6/2016  Wu et al.

FOREIGN PATENT DOCUMENTS

WO         2014184143 A1     11/2014
WO         2015142675 A2      9/2015
WO     WO 2015142675    *     9/2015
WO         2016124930 A1      8/2016

OTHER PUBLICATIONS

Walseng et al., Scientific Reports, 7:10713, published Sep. 6, 2017 (Year: 2017).*
International Search Report and Written Opinion for International Application No. PCT/US2017/049385, dated Nov. 17, 2017. 9 pages.

* cited by examiner

*Primary Examiner* — Kimberly Ballard
*Assistant Examiner* — Stacey N MacFarlane
(74) *Attorney, Agent, or Firm* — Perkins Coie LLP; Viola Kung

(57) ABSTRACT

The present invention is directed to a chimeric antigen receptor (CAR) fusion protein comprising from N-terminus to C-terminus: (i) a single-chain variable fragment (scFv) comprising $V_H$ and $V_L$, wherein scFv binds to a tumor antigen, (ii) a transmembrane domain, (iii) a co-stimulatory domain of GITR intracellular domain, and (iv) an activating domain. In one embodiment, the tumor antigen is human epidermal growth factor receptor (EGFR), human mesothelin, or human CD19. CARs having GITR intracellular domain as a co-stimulatory domain have certain advantages over other traditional CAR co-stimulatory domains.

7 Claims, 12 Drawing Sheets

Specification includes a Sequence Listing.

SEQUENCE LISTING

```
<160> NUMBER OF SEQ ID NOS: 30

<210> SEQ ID NO 1
<211> LENGTH: 1590
<212> TYPE: DNA
<213> ORGANISM: Homo sapiens

<400> SEQUENCE: 1
tctagagccg ccaccatggc cttaccagtg accgccttgc tcctgccgct ggccttgctg      60
ctccacgccg ccaggccggc tagcgaagtg cagctggtgc agagcggcgc ggaagtgaaa     120
aaaccgggca gcagcgtgaa agtgagctgc aaagcgagcg gcggcacctt tagcagctat     180
gcgattagct gggtgcgcca ggcgccgggc cagggcctgg aatggatggg cggcattatt     240 ccgattttg gcaccgcgaa ctatgcgcag aaatttcagg gccgcgtgac cattaccgcg      300
gatgaaagca ccagcaccgc gtatatggaa ctgagcagcc tgcgcagcga agataccgcg     360
gtgtattatt gcgcgcgcga agaaggcccg tattgcagca gcaccagctg ctatggcgcg     420
tttgatattt ggggccaggg caccctggtg accgtgagca gcggtggcgg tggttctggt     480
ggcggtggtt ctggtggcgg tggttctcag agcgtgctga cccaggatcc ggcggtgagc     540
gtggcgctgg gccagaccgt gaaaattacc tgccagggcg atagcctgcg cagctatttt     600
gcgagctggt atcagcagaa accgggccag gcgccgaccc tggtgatgta tgcgcgcaac     660
gatcgcccgg cgggcgtgcc ggatcgcttt agcggcagca aaagcggcac cagcgcgagc     720
ctggcgatta gcggcctgca gagcgaagat gaagcggatt attattgcgc ggcgtgggat     780
gatagcctga cggctatct gtttggcgcg ggcaccaaac tgaccgtgct gctcgagaag      840
cccaccacga cgccagcgcc gcgaccacca caccggcgcc caccatcgc gtcgcagccc      900 ctgtccctgc gcccagaggc gagccggcca cggcggggg gcgcagtgca cacgagggggg    960 ctggacttcg ccagtgataa gccctttggg gtgctggtgg tggttggtgg agtcctggct    1020
tgctatagct tgctagtaac agtggccttt attattttct gggtgcagct tggactgcac    1080
atctggcagc tgaggagtca gtgcatgtgg ccccgagaga cccagctgct gctggaggtg    1140
ccgccgtcga ccgaagacgc cagaagctgc agttccccg aggaagagcg gggcgagcga    1200
tcggcagagg agaaggggcg gctgggagac ctgtgggtga gagtgaagtt cagcaggagc    1260
gcagacgccc ccgcgtacca gcagggccag aaccagctct ataacgagct caatctagga    1320
cgaagagagg agtacgatgt tttggacaag agacgtggcc gggaccctga gatggggggga   1380 aagccgcaga gaaggaagaa ccctcaggaa ggcctgtaca tgaactgca gaaagataag      1440 atggcggagg cctacagtga gattgggatg aaaggcgagc gccggagggg caaggggcac    1500
gatggccttt accagggtct cagtacagcc accaaggaca cctacgacgc ccttcacatg    1560
caggccctgc cccctcgcta ataggaattc                                     1590

<210> SEQ ID NO 2
```

<211> LENGTH: 521
<212> TYPE: PRT
<213> ORGANISM: Homo sapiens

<400> SEQUENCE: 2

```
Met Ala Leu Pro Val Thr Ala Leu Leu Leu Pro Leu Ala Leu Leu Leu
1               5                   10                  15

His Ala Ala Arg Pro Ala Ser Glu Val Gln Leu Val Gln Ser Gly Ala
            20                  25                  30

Glu Val Lys Lys Pro Gly Ser Ser Val Lys Val Ser Cys Lys Ala Ser
        35                  40                  45

Gly Gly Thr Phe Ser Ser Tyr Ala Ile Ser Trp Val Arg Gln Ala Pro
    50                  55                  60

Gly Gln Gly Leu Glu Trp Met Gly Gly Ile Ile Pro Ile Phe Gly Thr
65                  70                  75                  80

Ala Asn Tyr Ala Gln Lys Phe Gln Gly Arg Val Thr Ile Thr Ala Asp
                85                  90                  95

Glu Ser Thr Ser Thr Ala Tyr Met Glu Leu Ser Ser Leu Arg Ser Glu
            100                 105                 110

Asp Thr Ala Val Tyr Tyr Cys Ala Arg Glu Glu Gly Pro Tyr Cys Ser
        115                 120                 125

Ser Thr Ser Cys Tyr Gly Ala Phe Asp Ile Trp Gly Gln Gly Thr Leu
    130                 135                 140

Val Thr Val Ser Ser Gly Gly Gly Ser Gly Gly Gly Gly Ser Gly
145                 150                 155                 160

Gly Gly Gly Ser Gln Ser Val Leu Thr Gln Asp Pro Ala Val Ser Val
                165                 170                 175

Ala Leu Gly Gln Thr Val Lys Ile Thr Cys Gln Gly Asp Ser Leu Arg
            180                 185                 190

Ser Tyr Phe Ala Ser Trp Tyr Gln Gln Lys Pro Gly Gln Ala Pro Thr
        195                 200                 205

Leu Val Met Tyr Ala Arg Asn Asp Arg Pro Ala Gly Val Pro Asp Arg
    210                 215                 220

Phe Ser Gly Ser Lys Ser Gly Thr Ser Ala Ser Leu Ala Ile Ser Gly
225                 230                 235                 240

Leu Gln Ser Glu Asp Glu Ala Asp Tyr Tyr Cys Ala Ala Trp Asp Asp
                245                 250                 255

Ser Leu Asn Gly Tyr Leu Phe Gly Ala Gly Thr Lys Leu Thr Val Leu
            260                 265                 270

Leu Glu Lys Pro Thr Thr Thr Pro Ala Pro Arg Pro Pro Thr Pro Ala
        275                 280                 285

Pro Thr Ile Ala Ser Gln Pro Leu Ser Leu Arg Pro Glu Ala Ser Arg
    290                 295                 300

Pro Ala Ala Gly Gly Ala Val His Thr Arg Gly Leu Asp Phe Ala Ser
305                 310                 315                 320

Asp Lys Pro Phe Trp Val Leu Val Val Val Gly Gly Val Leu Ala Cys
                325                 330                 335

Tyr Ser Leu Leu Val Thr Val Ala Phe Ile Ile Phe Trp Val Gln Leu
            340                 345                 350

Gly Leu His Ile Trp Gln Leu Arg Ser Gln Cys Met Trp Pro Arg Glu
        355                 360                 365

Thr Gln Leu Leu Leu Glu Val Pro Pro Ser Thr Glu Asp Ala Arg Ser
    370                 375                 380

Cys Gln Phe Pro Glu Glu Glu Arg Gly Glu Arg Ser Ala Glu Glu Lys
```

```
                                385                 390                 395                 400
Gly Arg Leu Gly Asp Leu Trp Val Arg Val Lys Phe Ser Arg Ser Ala
                405                 410                 415

Asp Ala Pro Ala Tyr Gln Gln Gly Gln Asn Gln Leu Tyr Asn Glu Leu
                420                 425                 430

Asn Leu Gly Arg Arg Glu Glu Tyr Asp Val Leu Asp Lys Arg Arg Gly
                435                 440                 445

Arg Asp Pro Glu Met Gly Gly Lys Pro Gln Arg Arg Lys Asn Pro Gln
        450                 455                 460

Glu Gly Leu Tyr Asn Glu Leu Gln Lys Asp Lys Met Ala Glu Ala Tyr
465                 470                 475                 480

Ser Glu Ile Gly Met Lys Gly Glu Arg Arg Arg Gly Lys Gly His Asp
                485                 490                 495

Gly Leu Tyr Gln Gly Leu Ser Thr Ala Thr Lys Asp Thr Tyr Asp Ala
                500                 505                 510

Leu His Met Gln Ala Leu Pro Pro Arg
        515                 520

<210> SEQ ID NO 3
<211> LENGTH: 63
<212> TYPE: DNA
<213> ORGANISM: Homo sapiens

<400> SEQUENCE: 3
atggccttac cagtgaccgc cttgctcctg ccgctggcct tgctgctcca cgccgccagg    60
ccg                                                                  63

<210> SEQ ID NO 4
<211> LENGTH: 21
<212> TYPE: PRT
<213> ORGANISM: Homo sapiens

<400> SEQUENCE: 4

Met Ala Leu Pro Val Thr Ala Leu Leu Leu Pro Leu Ala Leu Leu Leu
1               5                   10                  15

His Ala Ala Arg Pro
            20

<210> SEQ ID NO 5
<211> LENGTH: 747
<212> TYPE: DNA
<213> ORGANISM: Homo sapiens

<400> SEQUENCE: 5
gaagtgcagc tggtgcagag cggcgcggaa gtgaaaaaac cgggcagcag cgtgaaagtg    60
agctgcaaag cgagcggcgg cacctttagc agctatgcga ttagctgggt gcgccaggcg   120
ccgggccagg gcctggaatg gatgggcggc attattccga ttttggcac cgcgaactat    180 gcgcagaaat ttcagggccg cgtgaccatt accgcgatg aaagcaccag caccgcgtat    240
atggaactga gcagcctgcg cagcgaagat accgcggtgt attattgcgc gcgcgaagaa   300
ggcccgtatt gcagcagcac cagctgctat ggcgcgtttg atatttgggg ccagggcacc   360
ctggtgaccg tgagcagcgg tggcggtggt tctggtggcg gtggttctgg tggcggtggt   420
tctcagagcg tgctgaccca ggatccggcg gtgagcgtgg cgctgggcca gaccgtgaaa   480
attacctgcc agggcgatag cctgcgcagc tattttgcga gctggtatca gcagaaaccg   540
ggccaggcgc cgaccctggt gatgtatgcg cgcaacgatc gcccggcggg cgtgccggat   600
```

```
cgctttagcg gcagcaaaag cggcaccagc gcgagcctgg cgattagcgg cctgcagagc    660
gaagatgaag cggattatta ttgcgcggcg tgggatgata gcctgaacgg ctatctgttt    720
ggcgcgggca ccaaactgac cgtgctg                                        747
```

<210> SEQ ID NO 6
<211> LENGTH: 249
<212> TYPE: PRT
<213> ORGANISM: Homo sapiens

<400> SEQUENCE: 6

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Gly Pro Tyr Cys Ser Ser Thr Ser Cys Tyr Gly Ala
            100                 105                 110

Phe Asp Ile Trp Gly Gln Gly Thr Leu Val Thr Val Ser Ser Gly Gly
        115                 120                 125

Gly Gly Ser Gly Gly Gly Gly Ser Gly Gly Gly Gly Ser Gln Ser Val
    130                 135                 140

Leu Thr Gln Asp Pro Ala Val Ser Val Ala Leu Gly Gln Thr Val Lys
145                 150                 155                 160

Ile Thr Cys Gln Gly Asp Ser Leu Arg Ser Tyr Phe Ala Ser Trp Tyr
                165                 170                 175

Gln Gln Lys Pro Gly Gln Ala Pro Thr Leu Val Met Tyr Ala Arg Asn
            180                 185                 190

Asp Arg Pro Ala Gly Val Pro Asp Arg Phe Ser Gly Ser Lys Ser Gly
        195                 200                 205

Thr Ser Ala Ser Leu Ala Ile Ser Gly Leu Gln Ser Glu Asp Glu Ala
    210                 215                 220

Asp Tyr Tyr Cys Ala Ala Trp Asp Asp Ser Leu Asn Gly Tyr Leu Phe
225                 230                 235                 240

Gly Ala Gly Thr Lys Leu Thr Val Leu
                245
```

<210> SEQ ID NO 7
<211> LENGTH: 147
<212> TYPE: DNA
<213> ORGANISM: Homo sapiens

<400> SEQUENCE: 7

```
aagcccacca cgacgccagc gccgcgacca ccaacaccgg cgcccaccat cgcgtcgcag    60
cccctgtccc tgcgcccaga ggcgagccgg ccagcggcgg ggggcgcagt gcacacgagg   120
gggctggact tcgccagtga taagccc                                       147
```

<210> SEQ ID NO 8

```
<211> LENGTH: 49
<212> TYPE: PRT
<213> ORGANISM: Homo sapiens

<400> SEQUENCE: 8

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ser Arg Pro Ala
            20                  25                  30

Ala Gly Gly Ala Val His Thr Arg Gly Leu Asp Phe Ala Ser Asp Lys
        35                  40                  45

Pro

<210> SEQ ID NO 9
<211> LENGTH: 81
<212> TYPE: DNA
<213> ORGANISM: Homo sapiens

<400> SEQUENCE: 9
ttttgggtgc tggtggtggt tggtggagtc ctggcttgct atagcttgct agtaacagtg    60
gcctttatta ttttctgggt g                                             81

<210> SEQ ID NO 10
<211> LENGTH: 27
<212> TYPE: PRT
<213> ORGANISM: Homo sapiens

<400> SEQUENCE: 10

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 11
<211> LENGTH: 174
<212> TYPE: DNA
<213> ORGANISM: Homo sapiens

<400> SEQUENCE: 11
cagcttggac tgcacatctg gcagctgagg agtcagtgca tgtggccccg agagacccag    60
ctgctgctgg aggtgccgcc gtcgaccgaa gacgccagaa gctgccagtt ccccgaggaa   120
gagcggggcg agcgatcggc agaggagaag gggcggctgg agacctgtg ggtg          174

<210> SEQ ID NO 12
<211> LENGTH: 58
<212> TYPE: PRT
<213> ORGANISM: Homo sapiens

<400> SEQUENCE: 12

Gln Leu Gly Leu His Ile Trp Gln Leu Arg Ser Gln Cys Met Trp Pro
1               5                   10                  15

Arg Glu Thr Gln Leu Leu Leu Glu Val Pro Pro Ser Thr Glu Asp Ala
            20                  25                  30

Arg Ser Cys Gln Phe Pro Glu Glu Glu Arg Gly Glu Arg Ser Ala Glu
        35                  40                  45

Glu Lys Gly Arg Leu Gly Asp Leu Trp Val
    50                  55

<210> SEQ ID NO 13
```

<211> LENGTH: 342
<212> TYPE: DNA
<213> ORGANISM: Homo sapiens

<400> SEQUENCE: 13

```
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatgggggg aaagccgaga aggaagaacc ctcaggaagg cctgtacaat   180
gaactgcaga aagataagat ggcggaggcc tacagtgaga ttgggatgaa aggcgagcgc   240
cggaggggca aggggcacga tggcctttac cagggtctca gtacagccac caaggacacc   300
tacgacgccc ttcacatgca ggccctgccc cctcgctaat ag                      342
```

<210> SEQ ID NO 14
<211> LENGTH: 114
<212> TYPE: PRT
<213> ORGANISM: Homo sapiens

<400> SEQUENCE: 14

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Glu Thr Gly
            35                  40                  45

Gly Lys Pro Arg Arg Lys Asn Pro Gln Glu Gly Leu Tyr Asn Glu Leu
        50                  55                  60

Gln Lys Asp Lys Met Ala Glu Ala Tyr Ser Glu Ile Gly Met Lys Gly
65                  70                  75                  80

Glu Arg Arg Arg Gly Lys Gly His Asp Gly Leu Tyr Gln Gly Leu Ser
                85                  90                  95

Thr Ala Thr Lys Asp Thr Tyr Asp Ala Leu His Met Gln Ala Leu Pro
            100                 105                 110

Pro Arg
```

<210> SEQ ID NO 15
<211> LENGTH: 5
<212> TYPE: PRT
<213> ORGANISM: Artificial Sequence
<220> FEATURE:
<223> OTHER INFORMATION: synthetic

<400> SEQUENCE: 15

```
Gly Gly Gly Gly Ser
1               5
```

<210> SEQ ID NO 16
<211> LENGTH: 125
<212> TYPE: PRT
<213> ORGANISM: Homo sapiens

<400> SEQUENCE: 16

```
Glu Val Gln Leu Val Gln Ser Gly Ala Glu Val Lys Lys Pro Gly Ser
1               5                   10                  15

Ser Val Lys Ser Cys Lys Ala Ser Gly Gly Thr Phe Ser Ser Tyr Ala
                20                  25                  30

Ile Ser Trp Val Arg Gln Ala Pro Gly Gln Gly Leu Glu Trp Val Gly
            35                  40                  45
```

Gly Ile Ile Pro Ile Phe Gly Thr Ala Asn Tyr Ala Gln Lys Phe Gln
    50                  55                  60

Gly Arg Val Lys Ile Thr Ala Asp Glu Ser Ala Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Glu Glu Gly Pro Tyr Cys Ser Ser Thr Cys Tyr Gly Ala Phe
            100                 105                 110

Asp Ile Trp Gly Gln Gly Thr Leu Val Thr Val Ser Ser
            115                 120                 125

<210> SEQ ID NO 17
<211> LENGTH: 375
<212> TYPE: DNA
<213> ORGANISM: Homo sapiens

<400> SEQUENCE: 17
gaagtgcagc tggtgcagag cggcgcggaa gtgaaaaaac cgggcagcag cgtgaaaagc    60
tgcaaagcga gcggcggcac ctttagcagc tatgcgatta gctgggtgcg ccaggcgccg   120
ggccagggcc tggaatgggt gggcggcatt attccgattt ttggcaccgc gaactatgcg   180
cagaaatttc agggccgcgt gaaaattacc gcggatgaaa gcgcgagcac cgcgtatatg   240
gaactgagca gcctgcgcag cgaagatacc gcggtgtatt attgcgcgcg cgaagaaggc   300
ccgtattgca gcagcaccag ctgctatggc gcgtttgata tttggggcca gggcaccctg   360
gtgaccgtga gcagc                                                   375

<210> SEQ ID NO 18
<211> LENGTH: 108
<212> TYPE: PRT
<213> ORGANISM: Homo sapiens

<400> SEQUENCE: 18

Gln Ser Val Leu Thr Gln Asp Pro Ala Val Ser Val Ala Leu Gly Gln
1               5                   10                  15

Thr Val Lys Ile Thr Cys Gln Gly Asp Ser Leu Arg Ser Tyr Leu Ala
                20                  25                  30

Ser Trp Tyr Gln Gln Lys Pro Gly Gln Ala Pro Thr Leu Val Thr Tyr
            35                  40                  45

Ala Arg Asn Asp Arg Pro Ala Gly Val Pro Asp Arg Phe Ser Gly Ser
        50                  55                  60

Lys Ser Gly Thr Ser Ala Ser Leu Ala Ile Ser Gly Leu Gln Ser Glu
65                  70                  75                  80

Asp Glu Ala Asp Tyr Tyr Cys Ala Ala Trp Asp Asp Ser Leu Asn Gly
                85                  90                  95

Tyr Leu Phe Gly Ala Gly Thr Lys Leu Thr Val Leu
            100                 105

<210> SEQ ID NO 19
<211> LENGTH: 324
<212> TYPE: DNA
<213> ORGANISM: Homo sapiens

<400> SEQUENCE: 19
cagagcgtgc tgacccagga tccggcggtg agcgtggcgc tgggccagac cgtgaaaatt    60
acctgccagg gcgatagcct gcgcagctat ctggcgagct ggtatcagca gaaaccgggc   120
caggcgccga cccctggtga cctatgcgcg caacgatcgcc cggcgggcgt gccggatcgc   180

```
tttagcggca gcaaaagcgg caccagcgcg agcctggcga ttagcggcct gcagagcgaa      240
gatgaagcgg attattattg cgcggcgtgg gatgatagcc tgaacggcta tctgtttggc      300
gcgggcacca aactgaccgt gctg                                             324
```

<210> SEQ ID NO 20
<211> LENGTH: 123
<212> TYPE: DNA
<213> ORGANISM: Homo sapiens

<400> SEQUENCE: 20

```
aggagtaaga ggagcaggct cctgcacagt gactacatga acatgactcc ccgccgcccc      60
gggcccaccc gcaagcatta ccagccctat gccccaccac gcgacttcgc agcctatcgc      120
tcc                                                                    123
```

<210> SEQ ID NO 21
<211> LENGTH: 41
<212> TYPE: PRT
<213> ORGANISM: Homo sapiens

<400> SEQUENCE: 21

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 22
<211> LENGTH: 126
<212> TYPE: DNA
<213> ORGANISM: Homo sapiens

<400> SEQUENCE: 22

```
aaacgggca gaaagaaact cctgtatata ttcaaacaac catttatgag accagtacaa      60
actactcaag aggaagatgg ctgtagctgc cgatttccag aagaagaaga aggaggatgt      120
gaactg                                                                 126
```

<210> SEQ ID NO 23
<211> LENGTH: 44
<212> TYPE: PRT
<213> ORGANISM: Homo sapiens

<400> SEQUENCE: 23

```
Lys Arg Gly Arg Lys Lys Leu Leu Tyr Ile Phe Lys Gln Pro Phe Met
1               5                   10                  15

Glu Thr Arg Pro Val Gln Thr Thr Gln Glu Glu Asp Gly Cys Ser Cys
            20                  25                  30

Arg Phe Pro Glu Glu Glu Glu Gly Gly Cys Glu Leu
        35                  40
```

<210> SEQ ID NO 24
<211> LENGTH: 1566
<212> TYPE: DNA
<213> ORGANISM: Homo sapiens

<400> SEQUENCE: 24

```
atggccttac cagtgaccgc cttgctcctg ccgctggcct tgctgctcca cgccgccagg      60
```

```
ccggctagcg aagtgcagct ggtgcagagc ggcgcggaag tgaaaaaacc gggcagcagc    120
gtgaaagtga gctgcaaagc gagcggcggc acctttagca gctatgcgat tagctgggtg    180
cgccaggcgc cgggccaggg cctggaatgg atgggcggca ttattccgat ttttggcacc    240
gcgaactatg cgcagaaatt tcagggccgc gtgaccatta ccgcggatga aagcaccagc    300
accgcgtata tggaactgag cagcctgcgc agcgaagata ccgcggtgta ttattgcgcg    360
cgcgaagaag cccgtatttg cagcagcacc agctgctatg gcgcgtttga tatttggggc    420
cagggcaccc tggtgaccgt gagcagcggt ggcggtggtt ctggtggcgg tggttctggt    480
ggcggtggtt ctcagagcgt gctgacccag gatccggcgg tgagcgtggc gctgggccag    540
accgtgaaaa ttacctgcca gggcgatagc ctgcgcagct attttgcgag ctggtatcag    600
cagaaaccgg gccaggcgcc gaccctggtg atgtatgcgc gcaacgatcg cccggcgggc    660
gtgccggatc gctttagcgg cagcaaaagc ggcaccagcg cgagcctggc gattagcggc    720
ctgcagagcg aagatgaagc ggattattat tgcgcggcgt gggatgatag cctgaacggc    780
tatctgtttg gcgcgggcac caaactgacc gtgctgctcg agaagcccac cacgacgcca    840
gcgccgcgac caccaacacc ggcgcccacc atcgcgtcgc agccctgtc cctgcgccca    900 gaggcgagcc ggccagcggc gggggggcgca gtgcacacga gggggctgga cttcgccagt    960
gataagccct ttgggtgct ggtggtggtt ggtggagtcc tggcttgcta tagcttgcta   1020
gtaacagtgg ccttattat tttctgggtg cagcttggac tgcacatctg cagctgagg   1080 agtcagtgca tgtggccccg agagacccag ctgctgctgg aggtgccgcc gtcgaccgaa   1140
gacgccagaa gctgccagtt ccccgaggaa gagcggggcg agcgatcggc agaggagaag   1200
gggcggctgg agacctgtg ggtgagagtg aagttcagca ggagcgcaga cgccccgcg    1260 taccagcagg ccagaaccca gctctataac gagctcaatc taggacgaag agaggagtac   1320
gatgttttgg acaagagacg tggccgggac cctgagatgg ggggaaagcc gcagagaagg   1380
aagaaccctc aggaaggcct gtacaatgaa ctgcagaaag ataagatggc ggaggcctac   1440
agtgagattg ggatgaaagg cgagcgccgg aggggcaagg ggcacgatgg cctttaccag   1500
ggtctcagta cagccaccaa ggacacctac gacgcccttc acatgcaggc cctgccccct   1560
cgctaa                                                              1566
```

<210> SEQ ID NO 25
<211> LENGTH: 521
<212> TYPE: PRT
<213> ORGANISM: Homo sapiens

<400> SEQUENCE: 25

```
Met Ala Leu Pro Val Thr Ala Leu Leu Leu Pro Leu Ala Leu Leu Leu
1               5                   10                  15

His Ala Ala Arg Pro Ala Ser Glu Val Gln Leu Val Gln Ser Gly Ala
            20                  25                  30

Glu Val Lys Lys Pro Gly Ser Ser Val Lys Val Ser Cys Lys Ala Ser
        35                  40                  45

Gly Gly Thr Phe Ser Ser Tyr Ala Ile Ser Trp Val Arg Gln Ala Pro
    50                  55                  60

Gly Gln Gly Leu Glu Trp Met Gly Gly Ile Ile Pro Ile Phe Gly Thr
65                  70                  75                  80

Ala Asn Tyr Ala Gln Lys Phe Gln Gly Arg Val Thr Ile Thr Ala Asp
                85                  90                  95

Glu Ser Thr Ser Thr Ala Tyr Met Glu Leu Ser Ser Leu Arg Ser Glu
```

```
                100             105             110
Asp Thr Ala Val Tyr Tyr Cys Ala Arg Glu Glu Gly Pro Tyr Cys Ser
            115             120             125
Ser Thr Ser Cys Tyr Gly Ala Phe Asp Ile Trp Gly Gln Gly Thr Leu
            130             135             140
Val Thr Val Ser Ser Gly Gly Gly Ser Gly Gly Gly Ser Gly
145             150             155             160
Gly Gly Gly Ser Gln Ser Val Leu Thr Gln Asp Pro Ala Val Ser Val
            165             170             175
Ala Leu Gly Gln Thr Val Lys Ile Thr Cys Gln Gly Asp Ser Leu Arg
            180             185             190
Ser Tyr Phe Ala Ser Trp Tyr Gln Gln Lys Pro Gly Gln Ala Pro Thr
            195             200             205
Leu Val Met Tyr Ala Arg Asn Asp Arg Pro Ala Gly Val Pro Asp Arg
            210             215             220
Phe Ser Gly Ser Lys Ser Gly Thr Ser Ala Ser Leu Ala Ile Ser Gly
225             230             235             240
Leu Gln Ser Glu Asp Glu Ala Asp Tyr Tyr Cys Ala Ala Trp Asp Asp
            245             250             255
Ser Leu Asn Gly Tyr Leu Phe Gly Ala Gly Thr Lys Leu Thr Val Leu
            260             265             270
Leu Glu Lys Pro Thr Thr Thr Pro Ala Pro Arg Pro Pro Thr Pro Ala
            275             280             285
Pro Thr Ile Ala Ser Gln Pro Leu Ser Leu Arg Pro Glu Ala Ser Arg
            290             295             300
Pro Ala Gly Gly Ala Val His Thr Arg Gly Leu Asp Phe Ala Ser
305             310             315             320
Asp Lys Pro Phe Trp Val Leu Val Val Val Gly Gly Val Leu Ala Cys
            325             330             335
Tyr Ser Leu Leu Val Thr Val Ala Phe Ile Ile Phe Trp Val Gln Leu
            340             345             350
Gly Leu His Ile Trp Gln Leu Arg Ser Gln Cys Met Trp Pro Arg Glu
            355             360             365
Thr Gln Leu Leu Leu Glu Val Pro Pro Ser Thr Glu Asp Ala Arg Ser
            370             375             380
Cys Gln Phe Pro Glu Glu Glu Arg Gly Glu Arg Ser Ala Glu Glu Lys
385             390             395             400
Gly Arg Leu Gly Asp Leu Trp Val Arg Val Lys Phe Ser Arg Ser Ala
            405             410             415
Asp Ala Pro Ala Tyr Gln Gln Gly Gln Asn Gln Leu Tyr Asn Glu Leu
            420             425             430
Asn Leu Gly Arg Arg Glu Glu Tyr Asp Val Leu Asp Lys Arg Arg Gly
            435             440             445
Arg Asp Pro Glu Met Gly Gly Lys Pro Gln Arg Arg Lys Asn Pro Gln
            450             455             460
Glu Gly Leu Tyr Asn Glu Leu Gln Lys Asp Lys Met Ala Glu Ala Tyr
465             470             475             480
Ser Glu Ile Gly Met Lys Gly Glu Arg Arg Arg Gly Lys Gly His Asp
            485             490             495
Gly Leu Tyr Gln Gly Leu Ser Thr Ala Thr Lys Asp Thr Tyr Asp Ala
            500             505             510
Leu His Met Gln Ala Leu Pro Pro Arg
            515             520
```

<210> SEQ ID NO 26
<211> LENGTH: 1563
<212> TYPE: DNA
<213> ORGANISM: Homo sapiens

<400> SEQUENCE: 26

```
atggccttac cagtgaccgc cttgctcctg ccgctggcct tgctgctcca cgccgccagg      60
ccggctagcg acatccagat gacacagact acatcctccc tgtctgcctc tctgggagac     120
agagtcacca tcagttgcag ggcaagtcag gacattagta atatttaaa ttggtatcag      180
cagaaaccag atggaactgt taaactcctg atctaccata tcaagatt acactcagga      240
gtcccatcaa ggttcagtgg cagtgggtct ggaacagatt attctctcac cattagcaac     300
ctggagcaag aagatattgc cacttacttt tgccaacagg gtaatacgct tccgtacacg     360
ttcggagggg ggactaagtt ggaaataaca ggctccacct ctggatccgg caagcccgga     420
tctggcgagg gatccaccaa gggcgaggtg aaactgcagg agtcaggacc tggcctggtg     480
gcgccctcac agagcctgtc cgtcacatgc actgtctcag gggtctcatt acccgactat     540
ggtgtaagct ggattcgcca gcctccacga aagggtctgg agtggctggg agtaatatgg     600
ggtagtgaaa ccacatacta taattcagct ctcaaatcca gactgaccat catcaaggac     660
aactccaaga gccaagtttt cttaaaaatg aacagtctgc aaactgatga cacagccatt     720
tactactgtg ccaaacatta ttactacggt ggtagctatg ctatggacta ctggggtcaa     780
ggaacctcag tcaccgtctc ctcagcggcc gcactcgaga agcccaccac gacgccagcg     840
ccgcgaccac caacaccggc gcccaccatc gcgtcgcagc ccctgtccct gcgcccagag     900
gcgagccggc cagcggcggg gggcgcagtg cacacgaggg ggctggactt cgccagtgat     960
aagccctttt gggtgctggt ggtggttggt ggagtcctgg cttgctatag cttgctagta    1020
acagtggcct ttattatttt ctgggtgcag cttggactgc acatctggca gctgaggagt    1080
cagtgcatgt ggccccgaga gacccagctg ctgctggagt gccgccgtc gaccgaagac    1140
gccagaagct gccagttccc cgaggaagag cggggcgagc gatcggcaga ggagaagggg    1200
cggctgggag acctgtgggt gagagtgaag ttcagcagga gcgcagacgc ccccgcgtac    1260
cagcagggcc agaaccagct ctataacgag ctcaatctag gacgaagaga ggagtacgat    1320
gttttggaca gagacgtggc cgggacccct gagatggggg gaaagccgca gagaaggaag    1380
aaccctcagg aaggcctgta caatgaactg cagaaagata agatggcgga ggcctacagt    1440
gagattggga tgaaaggcga gcgccggagg ggcaaggggc acgatggcct ttaccagggt    1500
ctcagtacag ccaccaagga cacctacgac gcccttcaca tgcaggccct gccccctcgc    1560
taa                                                                  1563
```

<210> SEQ ID NO 27
<211> LENGTH: 520
<212> TYPE: PRT
<213> ORGANISM: Homo sapiens

<400> SEQUENCE: 27

```
Met Ala Leu Pro Val Thr Ala Leu Leu Leu Pro Leu Ala Leu Leu Leu
1               5                   10                  15

His Ala Ala Arg Pro Ala Ser Asp Ile Gln Met Thr Gln Thr Thr Ser
            20                  25                  30

Ser Leu Ser Ala Ser Leu Gly Asp Arg Val Thr Ile Ser Cys Arg Ala
        35                  40                  45
```

```
Ser Gln Asp Ile Ser Lys Tyr Leu Asn Trp Tyr Gln Gln Lys Pro Asp
    50                  55                  60
Gly Thr Val Lys Leu Leu Ile Tyr His Thr Ser Arg Leu His Ser Gly
65                  70                  75                  80
Val Pro Ser Arg Phe Ser Gly Ser Gly Ser Gly Thr Asp Tyr Ser Leu
                85                  90                  95
Thr Ile Ser Asn Leu Glu Gln Glu Asp Ile Ala Thr Tyr Phe Cys Gln
                100                 105                 110
Gln Gly Asn Thr Leu Pro Tyr Thr Phe Gly Gly Gly Thr Lys Leu Glu
                115                 120                 125
Ile Thr Gly Ser Thr Ser Gly Ser Gly Lys Pro Gly Ser Gly Glu Gly
        130                 135                 140
Ser Thr Lys Gly Glu Val Lys Leu Gln Glu Ser Gly Pro Gly Leu Val
145                 150                 155                 160
Ala Pro Ser Gln Ser Leu Ser Val Thr Cys Thr Val Ser Gly Val Ser
                165                 170                 175
Leu Pro Asp Tyr Gly Val Ser Trp Ile Arg Gln Pro Pro Arg Lys Gly
                180                 185                 190
Leu Glu Trp Leu Gly Val Ile Trp Gly Ser Glu Thr Thr Tyr Tyr Asn
            195                 200                 205
Ser Ala Leu Lys Ser Arg Leu Thr Ile Ile Lys Asp Asn Ser Lys Ser
        210                 215                 220
Gln Val Phe Leu Lys Met Asn Ser Leu Gln Thr Asp Asp Thr Ala Ile
225                 230                 235                 240
Tyr Tyr Cys Ala Lys His Tyr Tyr Tyr Gly Gly Ser Tyr Ala Met Asp
                245                 250                 255
Tyr Trp Gly Gln Gly Thr Ser Val Thr Val Ser Ser Ala Ala Ala Leu
            260                 265                 270
Glu Lys Pro Thr Thr Thr Pro Ala Pro Arg Pro Pro Thr Pro Ala Pro
        275                 280                 285
Thr Ile Ala Ser Gln Pro Leu Ser Leu Arg Pro Glu Ala Ser Arg Pro
        290                 295                 300
Ala Ala Gly Gly Ala Val His Thr Arg Gly Leu Asp Phe Ala Ser Asp
305                 310                 315                 320
Lys Pro Phe Trp Val Leu Val Val Val Gly Gly Val Leu Ala Cys Tyr
                325                 330                 335
Ser Leu Leu Val Thr Val Ala Phe Ile Ile Phe Trp Val Gln Leu Gly
            340                 345                 350
Leu His Ile Trp Gln Leu Arg Ser Gln Cys Met Trp Pro Arg Glu Thr
        355                 360                 365
Gln Leu Leu Leu Glu Val Pro Pro Ser Thr Glu Asp Ala Arg Ser Cys
        370                 375                 380
Gln Phe Pro Glu Glu Glu Arg Gly Glu Arg Ser Ala Glu Lys Gly
385                 390                 395                 400
Arg Leu Gly Asp Leu Trp Val Arg Val Lys Phe Ser Arg Ser Ala Asp
                405                 410                 415
Ala Pro Ala Tyr Gln Gln Gly Gln Asn Gln Leu Tyr Asn Glu Leu Asn
                420                 425                 430
Leu Gly Arg Arg Glu Glu Tyr Asp Val Leu Asp Lys Arg Arg Gly Arg
        435                 440                 445
Asp Pro Glu Met Gly Gly Lys Pro Gln Arg Arg Lys Asn Pro Gln Glu
        450                 455                 460
```

```
Gly Leu Tyr Asn Glu Leu Gln Lys Asp Lys Met Ala Glu Ala Tyr Ser
465                 470                 475                 480

Glu Ile Gly Met Lys Gly Glu Arg Arg Gly Lys Gly His Asp Gly
            485                 490                 495

Leu Tyr Gln Gly Leu Ser Thr Ala Thr Lys Asp Thr Tyr Asp Ala Leu
            500                 505                 510

His Met Gln Ala Leu Pro Pro Arg
            515                 520

<210> SEQ ID NO 28
<211> LENGTH: 24
<212> TYPE: PRT
<213> ORGANISM: Homo sapiens

<400> SEQUENCE: 28

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 29
<211> LENGTH: 1509
<212> TYPE: DNA
<213> ORGANISM: Homo sapiens

<400> SEQUENCE: 29
```

| | | | | |
|---|---|---|---|---|
| atggccttac cagtgaccgc cttgctcctg ccgctggcct tgctgctcca cgccgccagg | 60 |
| ccggacatcc agatgacaca gactacatcc tccctgtctg cctctctggg agacagagtc | 120 |
| accatcagtt gcagggcaag tcaggacatt agtaaatatt taaattggta tcagcagaaa | 180 |
| ccagatggaa ctgttaaact cctgatctac catacatcaa gattacactc aggagtccca | 240 |
| tcaaggttca gtggcagtgg gtctggaaca gattattctc tcaccattag caacctggag | 300 |
| caagaagata ttgccactta cttttgccaa cagggtaata cgcttccgta cacgttcgga | 360 |
| gggggactaa gttggaaat aacaggtggc ggtggcagcg gcggtggtgg ttccggaggc | 420 |
| ggcggttctg aggtgaaact gcaggagtca ggacctggcc tggtggcgcc ctcacagagc | 480 |
| ctgtccgtca catgcactgt ctcaggggtc tcattacccg actatggtgt aagctggatt | 540 |
| cgccagcctc cacgaaaggg tctggagtgg ctgggagtaa tatggggtag tgaaaccaca | 600 |
| tactataatt cagctctcaa atccagactg accatcatca aggacaactc caagagccaa | 660 |
| gttttcttaa aaatgaacag tctgcaaact gatgacacag ccatttacta ctgtgccaaa | 720 |
| cattattact acggtggtag ctatgctatg gactactggg gtcaaggaac ctcagtcacc | 780 |
| gtctcctcaa ccacgacgcc agcgccgcga ccaccaacac cggcgcccac catcgcgtcg | 840 |
| cagcccctgt ccctgcgccc agaggcgtgc cggccagcgg cggggggcgc agtgcacacg | 900 |
| agggggctgg acttcgcctg tgatatctac atctgggcgc ccctggccgg acttgtgggg | 960 |
| gtccttctcc tgtcactggt tatcacccTt tactgccagc ttggactgca catctggcag | 1020 |
| ctgaggagtc agtgcatgtg gccccgagag acccagctgc tgctggaggt ccgccgtcg | 1080 |
| accgaagacg ccagaagctg ccagttcccc gaggaagagc ggggcgagcg atcggcagag | 1140 |
| gagaagggc ggctgggaga cctgtgggtg agagtgaagt tcagcaggag cgcagacgcc | 1200 |
| cccgcgtaca agcagggcca gaaccagctc tataacgagc tcaatctagg acgaagagag | 1260 |
| gagtacgatg ttttggacaa gagacgtggc cgggaccctg agatgggggg aaagccgaga | 1320 |
| aggaagaacc ctcaggaagg cctgtacaat gaactgcaga agataagat ggcggaggcc | 1380 |

```
tacagtgaga ttgggatgaa aggcgagcgc cggaggggca aggggcacga tggcctttac    1440
cagggtctca gtacagccac caaggacacc tacgacgccc ttcacatgca ggccctgccc    1500
cctcgctaa                                                            1509
```

<210> SEQ ID NO 30
<211> LENGTH: 504
<212> TYPE: PRT
<213> ORGANISM: Homo sapiens

<400> SEQUENCE: 30

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Gln Leu Gly Leu
                325                 330                 335

His Ile Trp Gln Leu Arg Ser Gln Cys Met Trp Pro Arg Glu Thr Gln
```

-continued

```
            340                 345                 350
Leu Leu Leu Glu Val Pro Pro Ser Thr Glu Asp Ala Arg Ser Cys Gln
            355                 360                 365

Phe Pro Glu Glu Glu Arg Gly Glu Arg Ser Ala Glu Glu Lys Gly Arg
        370                 375                 380

Leu Gly Asp Leu Trp Val Arg Val Lys Phe Ser Arg Ser Ala Asp Ala
385                 390                 395                 400

Pro Ala Tyr Lys Gln Gly Gln Asn Gln Leu Tyr Asn Glu Leu Asn Leu
                405                 410                 415

Gly Arg Arg Glu Glu Tyr Asp Val Leu Asp Lys Arg Arg Gly Arg Asp
                420                 425                 430

Pro Glu Met Glu Thr Gly Gly Lys Pro Arg Arg Lys Asn Pro Gln Glu
            435                 440                 445

Gly Leu Tyr Asn Glu Leu Gln Lys Asp Lys Met Ala Glu Ala Tyr Ser
        450                 455                 460

Glu Ile Gly Met Lys Gly Glu Arg Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495

His Met Gln Ala Leu Pro Pro Arg
                500
```

CHIMERIC ANTIGEN RECEPTORS HAVING GITR INTRACELLULAR DOMAIN AS CO-STIMULATORY DOMAIN

This application is a continuation of PCT/US2017/049385, filed Aug. 30, 2017; which claims the priority of U.S. Provisional Application No. 62/381,418, filed Aug. 30, 2016. The contents of the above-identified applications are incorporated herein by reference in their entireties.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Aug. 30, 2017, and a size of 38.7 kilobytes. The Sequence Listing filed via EFS-Web is part of the specification and is hereby incorporated in its entirety by reference herein.

FIELD OF THE INVENTION

The present invention relates to chimeric antigen receptors (CARs) having GITR intracellular domain as a co-stimulatory domain. which effectively attack tumor cells overexpressing a tumor antigen such as EGFR, mesothelin, or CD19, and not against cancer cells that do not express such a tumor antigen.

BACKGROUND OF THE INVENTION

Immunotherapy is emerging as a highly promising approach for the treatment of cancer. T cells or T lymphocytes, the armed forces of our immune system, constantly look for foreign antigens and discriminate abnormal (cancer or infected cells) from normal cells. Genetically modifying T cells with CARs is the most common approach to design tumor-specific T cells. CAR-T cells targeting tumor-associated antigens (TAA) can be infused into patients (called adoptive cell transfer or ACT) representing an efficient immunotherapy approach [1, 2]. The advantage of CAR-T technology compared with chemotherapy or antibody is that reprogrammed engineered T cells can proliferate and persist in the patient ("a living drug")[3], [4].

CARs

CARs (Chimeric antigen receptors) usually consist of a monoclonal antibody-derived single-chain variable fragment (scFv) linked by a hinge and transmembrane domain to a variable number of intracellular signaling domains: (i) a single, cellular activating, CD3-zeta domain; or (ii) CD28 or CD137 (4-1BB) as a co-stimulatory domain, in tandem with a CD3-zeta domain. (FIG. 1). The CD27 signaling domain has also been used in the place of either the CD28 or CD137 domain)[1, 2]. The evolution of CARs went from first generation (with no costimulation domain) to second generation (with one co-stimulation domain) to third generation CAR (with several costimulation domains). Generating CARs with multiple costimulatory domains (the so-called $3^{rd}$ generation CAR) have led to increased cytolytic activity, and significantly improved persistence of CAR-T cells that demonstrate augmented antitumor activity. The CAR structure is shown in FIG. 1.

CAR-T cells are effectively used in clinical trials against hematological cancer targets [6]. Recently, CAR-T cells were used against solid tumors against mesothelin, EGFR, Her-2 or other targets [5, 7]. Affinity-tuned Her-2 and EGFR showed high specificity against cancer cells versus normal cells, providing higher safety for CAR-T therapy [5].

EGFR

EGFR is an epidermal growth factor receptor that is overexpressed in many types of cancer [3]. EGFR is one of the four receptor tyrosine kinases of Erb family such as ErbB2/HER-2, ErbB3/HER3 and ErbB4/HER4 [3]. EGFR plays important function in proliferation, growth regulation, angiogenesis, survival and metastasis.

EFGR contains 4 extracellular domains, transmembrane domain, and intracellular domain containing tyrosine kinase domain and carboxy-terminal tail (FIG. 2). Many types of cancers such as glioblastoma and others have deletion of amino-acids 5-273 resulting in expression of EGFRvIII form [4]. Both forms of EGFR wild type and EGFRvIII are critical for tumor survival signaling.

EGFR is involved in regulation of MAP kinase, PI3K, AKT, STAT signaling pathways. There are many tyrosine kinase inhibitors were developed, and recently immunotherapy approaches to target EGFR signaling were developed [5].

Mesothelin

Mesothelin is a tumor surface antigen that is highly overexpressed in many types of tumors [8], including ovarian tumors [9]. Mesothelin-CD28-CD3 zeta CAR-T cells have been shown to kill ovarian tumors [10].

CD19

Cluster of differentiation 19 (CD19) is a protein encoded by the CD19 gene, and is a B-lymphocyte antigen found on the surface of B-cells. CD19 is highly expressed in many types of hematologic cancers [2, 6, 11, 12]. CD19-CD28-CD3 zeta and CD19-4-1BB-CD3 zeta CAR-T cells have been shown to kill hematological cancers [13]. Many CD19-CAR-T cell clinical trials demonstrated promising results in clinic with this type of therapy[14].

BRIEF DESCRIPTION OF THE DRAWINGS

FIG. 6A-6D show the cytotoxic activities of EGFR-CAR with different co-stimulatory domains in different cancer cell lines with high expression of EGFR. FIG. 6E shows no cytotoxic activity of EGFR-CAR in MCF-7 cells, that were EGFR-1-negative. E:T, Effector to Target cell ratio.

DETAILED DESCRIPTION OF THE INVENTION

Definitions

Figure 1:
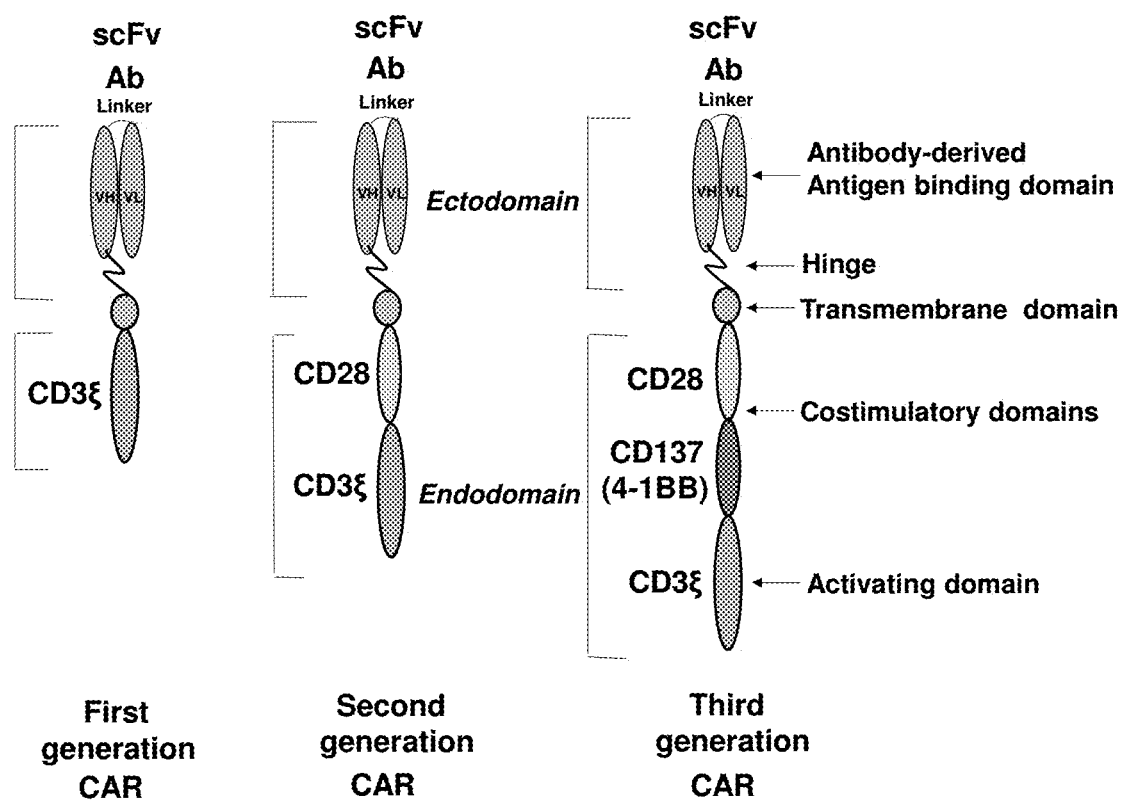
FIG. 1. The structure of CAR. On the left panel, the structure of first generation (no costimulation domains) is shown. In the middle panel, a second generation (one co-stimulation domain CD28) is shown. On the right panel, a third generation (two co-stimulation domains of CD28 and 4-1BB) is shown [7].
Figure 2:
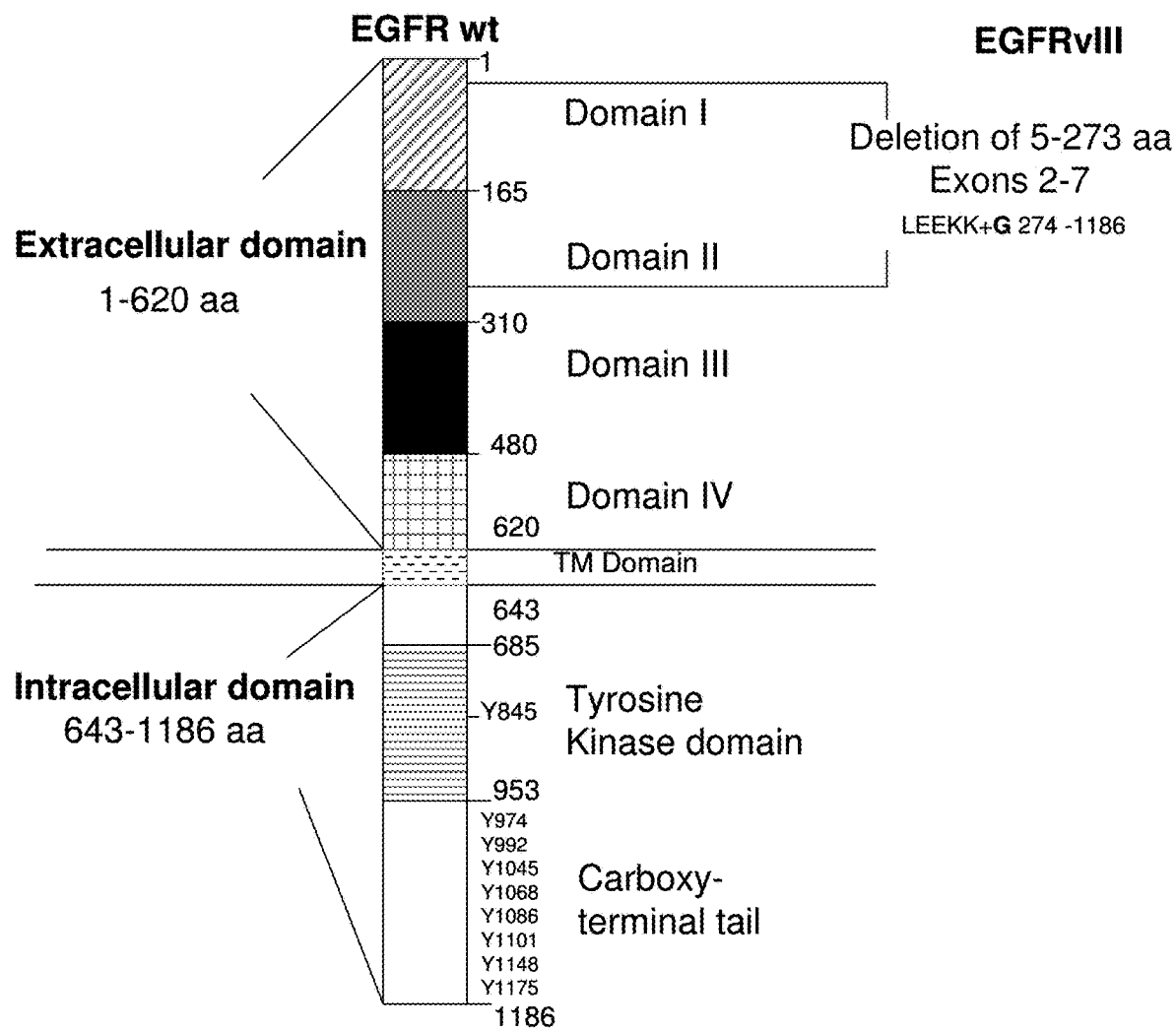
FIG. 2. The structure of EGFR and EGFRvIII proteins.

As used herein, "adoptive cell therapy" (ACT) is a treatment that uses a cancer patient's own T lymphocytes with anti-tumor activity, expanded in vitro and reinfused into the patient with cancer.

As used herein, "affinity" is the strength of binding of a single molecule to its ligand. Affinity is typically measured and reported by the equilibrium dissociation constant ($K_D$ or Kd), which is used to evaluate and rank order strengths of bimolecular interactions.

As used herein, a "chimeric antigen receptor (CAR)" means a fused protein comprising an extracellular domain capable of binding to an antigen, a transmembrane domain derived from a polypeptide different from a polypeptide from which the extracellular domain is derived, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell.

As used herein, a "domain" means one region in a polypeptide which is folded into a particular structure independently of other regions.

GITR (glucocorticoid-induced TNFR-related protein) is a surface receptor molecule that is known to induce T lymphocyte survival and inhibit suppressive activity of regulatory T cells [15]. GITR is a member of TNF family receptors. GITR is also known as tumor necrosis factor receptor superfamily member 18 (TNFRSF18), activation-inducible TNFR family receptor (AITR) and is a protein encoded by the TNFRSF18 gene in humans. GITR has 241 amino acids and its NCBI Reference Sequence Number is NP_004186.1. The intracellular domain of GITR (SEQ ID NO: 12) is used in the present invention, which is the amino acid residues 184-241 of NCBI Reference Sequence No. NP_004186.1).

As used herein, a "single chain variable fragment (scFv)" means a single chain polypeptide derived from an antibody which retains the ability to bind to an antigen. An example of the scFv includes an antibody polypeptide which is formed by a recombinant DNA technique and in which Fv regions of immunoglobulin heavy chain (H chain) and light chain (L chain) fragments are linked via a spacer sequence. Various methods for preparing an scFv are known to a person skilled in the art.

As used herein, a "tumor antigen" means a biological molecule having antigenicity, expression of which causes cancer.

Description

The inventors have discovered that GITR intracellular domain can replace other traditional co-stimulatory domains such as CD28 and 4-1BB in CAR and provides advantages in clinics. The inventors have demonstrated that CARs having GITR intracellular domain as a co-stimulatory domain activate CAR-T cells to express ScFv of EGFR, mesothelin, or CD19, and kills EGFR-, mesothelin-, or CD19-positive cells. GITR intracellular domain as a co-stimulatory domain provides advantages over CD28 or 4-1BB, because GITR can provide dual functions of (i) inducing T cell effector function and activating T cells, and (ii) suppressing inhibitory T regulatory cells that block immune response. GITR intracellular domain-containing CAR T cells can decrease the production of cytokines, which results in less cytokine release syndrome (CRS).

The present invention provides CAR-T cells that target a tumor antigen which is highly overexpressed in many types of cancer such as breast cancer, pancreatic cancer, glioblastoma, ovarian cancer, and hematologic cancers (leukemia, lymphoma, multiple myeloma). The inventors use (i) an antibody that specifically recognizes a tumor antigen-expressing cancer cells to prepare scFv, and (ii) GITR intracellular domain as a co-stimulatory domain, to generate GITR-CAR-T cells. The inventors have demonstrated that several GITR-CD3 zeta-CAR-T cells of the present invention have high cytotoxic activity against several cancer cells with high tumor antigen expression and have no activity in tumor antigen-negative cells.

The present invention provides a chimeric antigen receptor fusion protein comprising from N-terminus to C-terminus: (i) a single-chain variable fragment (scFv) having activity against a tumor antigen, (ii) a transmembrane domain, (iii) a GITR intracellular domain as a co-stimulatory domain, and (iv) an activating domain.

In one embodiment, the human tumor antigen is selected from the group consisting of: EGFR, mesothelin, CD19, CD20, BCMA, CD22, CD38, CD138, VEGFR-2, CD4, CD5, CD30, CD22, CD24, CD25, CD28, CD30, CD33, CD47, CD52, CD56, CD80, CD81, CD86, CD123, CD171, CD276, B7H4, CD133, GPC3; PMSA, CD3, CEACAM6, c-Met, EGFRvIII, ErbB2/HER-2, ErbB3/HER3, ErbB4/HER-4, EphA2,10a, IGF1R, GD2, O-acetyl GD2, O-acetyl GD3, GHRHR, GHR, FLT1, KDR, FLT4, CD44v6, CD151, CA125, CEA, CTLA-4, GITR, BTLA, TGFBR2, TGFBR1, IL6R, gp130, Lewis A, Lewis Y, NGFR, MCAM, TNFR1, TNFR2, PD1, PD-L1, PD-L2, HVEM, MAGE-A, NY-ESO-1, PSMA, RANK, ROR1, ROR-2, TNFRSF4, CD40, CD137, TWEAK-R, LTPR, LIFRP, LRPS, MUC1, TCRa, TCRp, TLR7, TLR9, PTCH1, WT-1, Robol, a, Frizzled, OX40, CD79b, and Notch-1-4. Preferred tumor antigens are human EGFR, human mesothelin, and human CD19.

The CAR of the present invention comprises a single chain variable fragment (scFv) that binds specifically to the tumor antigen of interest. The heavy chain (H chain) and light chain (L chain) fragments of an antibody are linked via a linker sequence. For example, a linker can be 5-20 amino acids. The scFv structure can be VL-linker-VH, or VH-linker-VL, from N-terminus to C-terminus.

The CAR of the present invention comprises a transmembrane domain which spans the membrane. The transmembrane domain may be derived from a natural polypeptide, or may be artificially designed. The transmembrane domain derived from a natural polypeptide can be obtained from any membrane-binding or transmembrane protein. For example, a transmembrane domain of a T cell receptor α or β chain, CD28, CD3-epsilon, CD45, CD4, CD5, CD8, CD9, CD16, CD22, CD33, CD37, CD64, CD80, CD86, CD134, CD137, ICOS, CD154, or a GITR can be used. The artificially designed transmembrane domain is a polypeptide mainly comprising hydrophobic residues such as leucine and valine. It is preferable that a triplet of phenylalanine, tryptophan and valine is found at each end of the synthetic transmembrane domain. In preferred embodiments, the transmembrane domain is derived from CD28 or CD8, which give good receptor stability.

The CAR of the present invention comprises a GITR intracellular domain as a co-stimulatory domain.

The endodomain (the activating domain) is the signal-transmission portion of the CAR. After antigen recognition, receptors cluster and a signal is transmitted to the cell. The most commonly used endodomain component is that of CD3 zeta (CD3 Z or CD3ζ), which contains 3 ITAMs. This transmits an activation signal to the T cell after antigen is bound.

The CAR fusion protein may comprise a FLAG tag located at N-terminus to scFv, or C-terminus to scFv, or between $V_H$ and $V_L$. The FLAG tag needs to be in extracellular domain, and not in the intracellular domain. In addition to FLAG tag, other tags may be used in the construct. FLAG tag is a preferred tag because it does not cause immunogenicity and has decreased level of cytokine secretion.

The CAR of the present invention may comprise a signal peptide N-terminal to the scFv so that when the CAR is expressed inside a cell, such as a T-cell, the nascent protein is directed to the endoplasmic reticulum and subsequently to the cell surface, where it is expressed. The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases. As an example, the signal peptide may derive from human CD8 or GM-CSF, or a variant thereof having 1 or 2 amino acid mutations provided that the signal peptide still functions to cause cell surface expression of the CAR.

The CAR of the present invention may comprise a spacer sequence as a hinge to connect scFv with the transmembrane domain and spatially separate antigen binding domain from the endodomain. A flexible spacer allows to the binding domain to orient in different directions to enable its binding to a tumor antigen. The spacer sequence may, for example, comprise an IgG1 Fc region, an IgG1 hinge or a CD8 stalk, or a combination thereof. A human CD28 or CD8 stalk is preferred.

Figure 3:
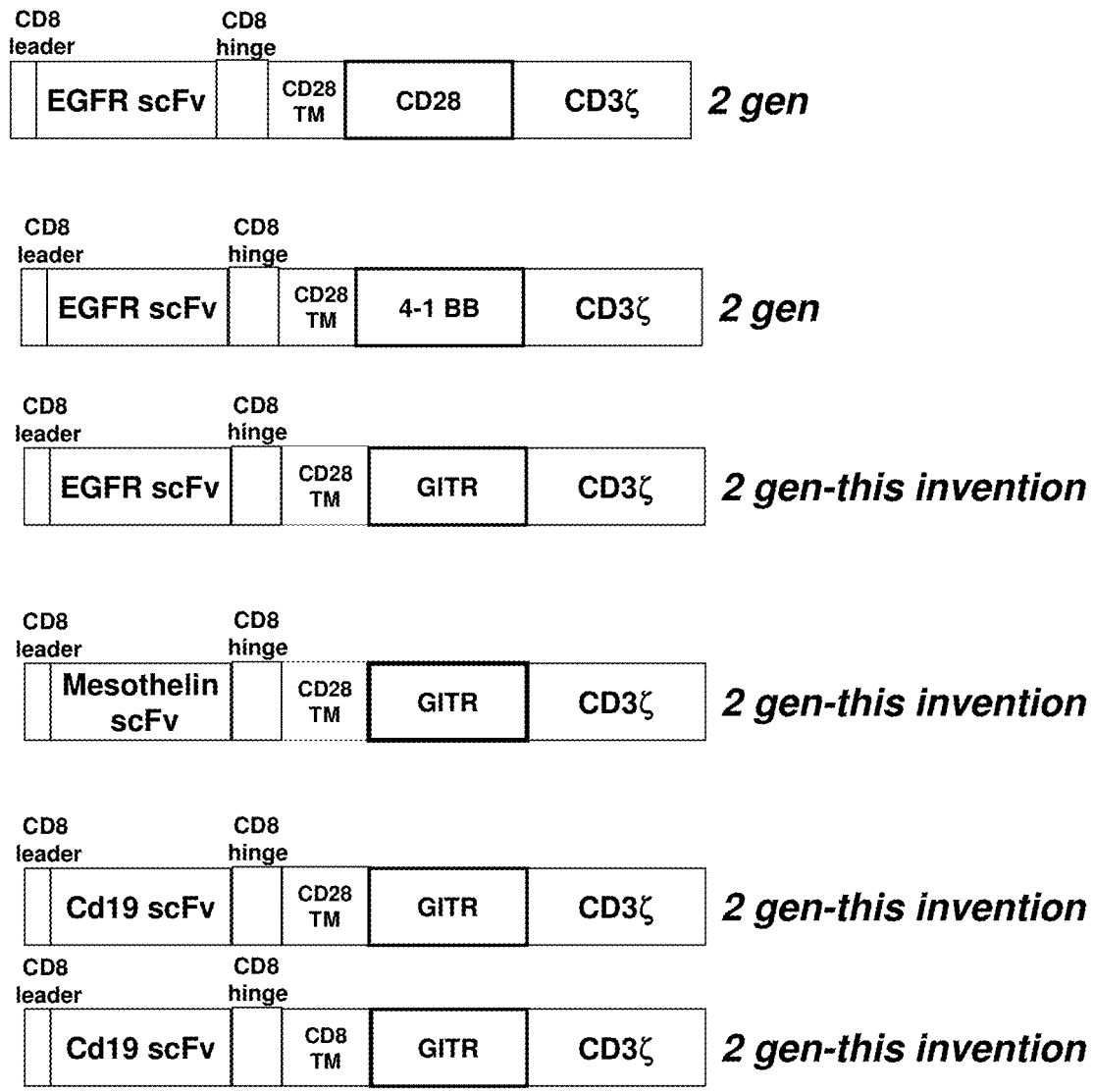
FIG. 3. The structures of EGFR-CAR, mesothelin-CAR and CD19-CAR constructs. The present invention uses GITR as co-stimulatory domain.

FIG. 3 shows the structure of EGFR, mesothelin, or CD19 CAR constructs. The second generation of CAR-T constructs are used. The co-stimulatory domains are CD28 (comparison), 4-1BB (comparison), or GITR intracellular domain (this invention). CD19-GITR-CD3 zeta are designed with CD8 and CD28 trans-membrane domain.

The present invention provides a nucleic acid encoding the CAR described above. The nucleic acid encoding the CAR can be prepared from an amino acid sequence of the specified CAR by a conventional method. A base sequence encoding an amino acid sequence can be obtained from the aforementioned NCBI RefSeq IDs or accession numbers of GenBenk for an amino acid sequence of each domain, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

The nucleic acid encoding the CAR of the present invention can be inserted into a vector, and the vector can be introduced into a cell. For example, a virus vector such as a retrovirus vector (including a lentivirus vector, an oncoretrovirus vector, and a pseudo type vector), an adenovirus vector, an adeno-associated virus (AAV) vector, a simian virus vector, a vaccinia virus vector or a Sendai virus vector, an Epstein-Barr virus (EBV) vector, and a HSV vector can be used. As the virus vector, a virus vector lacking the replicating ability so as not to self-replicate in an infected cell is preferably used.

For example, when a retrovirus vector is used, the process of the present invention can be carried out by selecting a suitable packaging cell based on a LTR sequence and a packaging signal sequence possessed by the vector and preparing a retrovirus particle using the packaging cell. Examples of the packaging cell include PG13 (ATCC CRL-10686), PA317 (ATCC CRL-9078), GP+E-86 and GP+en-vAm-12, and Psi-Crip. A retrovirus particle can also be prepared using a 293 cell or a 293T cell having high transfection efficiency. Many kinds of retrovirus vectors produced based on retroviruses and packaging cells that can be used for packaging of the retrovirus vectors are widely commercially available from many companies.

The present invention provides T cells modified to express the chimeric antigen receptor fusion protein as described above. CAR-T cells of the present invention bind to a specific antigen via the CAR, thereby a signal is transmitted into the cell, and as a result, the cell is activated. The activation of the cell expressing the CAR is varied depending on the kind of a host cell and an intracellular domain of the CAR, and can be confirmed based on, for example, release of a cytokine, improvement of a cell proliferation rate, change in a cell surface molecule, or the like as an index.

T cells modified to express the CAR can be used as a therapeutic agent for a disease. The therapeutic agent comprises the T cells expressing the CAR as an active ingredient, and may further comprise a suitable excipient. Examples of the excipient include pharmaceutically acceptable excipients known to a person skilled in the art.

In one embodiment, the EGFR scFv useful in the present invention has a low affinity against human EFGR, i.e., it has a dissociation constant $(K_D) > 50$ nM, or $>80$ nM, or $>100$ nM, or $>150$ nM, and preferably $\geq 200$ nM or 250 nM. In one embodiment, the scFv is derived from C10 or P3-5 (see References 5 and 8) or has at least 90% sequence identity, as that of C10 or P3-5. Preferably, the scFv has at least 92%, 95%, 98%, or 99% sequence identity, as that of C10 or P3-5. CAR-T cells with low affinity scFv to EGFR exhibits robust antitumor efficacy similar to high-affinity antibody cells, but spared normal cells expressing physiologic EGFR levels, and thus they increase the therapeutic index.

In one embodiment, the mesothelin scFv useful in the present invention is derived from the anti-mesothelin antibody reported by Lanitis et al [17].

In one embodiment, the CD19 scFv useful in the present invention is derived from the anti-CD19 antibody reported by Kochenderfer et al [18].

GITR intracellular domain belongs to TNFR superfamily (TNFRSF) protein family and is a co-stimulatory domain for activating T cells. The inventors have discovered the following advantages of using GITR for CAR-T therapy. GITR-GITRL interaction mediates effective anti-tumor immune responses, by promoting expansion and activation of effector T cell populations and by suppressing T regulatory cells that suppress immune activity. The dual function of GITR to activate effector cells and to inhibit the repressing functions of T regulatory cells makes it effective for CAR-T immunotherapy.

This invention demonstrates construction of lentiviral EGFR-GITR-CD3 zeta containing vector and EGFR-GITR-CAR-T cells; lentiviral mesothelin-GITR-CD3 zeta containing vector and mesothelin-GITR-CAR-T cells; lentiviral CD19-GITR-CD3 zeta containing vector and CD19-GITR-CD3 zeta CAR-T cells.

The present invention provides a CAR fusion protein having the amino acid sequence of SEQ ID NO: 2, 25, or 27, or a sequence having at least 95%, or 97%, or 99% sequence identity thereof.

The present invention provides a nucleic acid encoding a CAR fusion protein, the nucleic acid has the sequence of SEQ ID NO: 1, 24, or 26, or a sequence having at least 95%, or 97%, or 99% sequence identity thereof.

The present invention provides an adoptive cell therapy method for treating cancer, comprising the step of administering EGFR-GITR-CD3 zeta CAR-T cells to a subject suffering from cancer.

The present invention provides an adoptive cell therapy method for treating cancer, comprising the step of administering mesothelin-GITR-CD3 zeta CAR-T cells to a subject suffering from cancer.

The present invention provides an adoptive cell therapy method for treating cancer, comprising the step of administering CD19-GITR-CD3 zeta CAR-T cells to a subject suffering from cancer.

In one embodiment, low affinity EGFR antibody and a GITR intracellular domain as a co-stimulatory domain are used to prepare the EFGR-GITR CAR-T cells construct. EGFR scFv (e.g., from low affinity antibody C10 or P3-5 [16]) is cloned into Xba I and EcoR I sites of lentiviral vector. The CAR construct contains CD8 signaling peptide, EGFR scFv: VH-(variable heavy chain)-linker 3-VL (variable light chain) from low affinity EGFR antibody, CD8 hinge, CD28 transmembrane domain, GITR intracellular domain and CD3 zeta activation domains.

The inventors have generated EGFR-scFv-GITR-CD3 zeta-CAR-T cells against EGFR-positive cancer cell lines such as breast, ovarian, pancreatic, brain cancer and others. The inventors have provided data demonstrating efficient expansion of the EGFR-GITR CAR-T cells in culture. EGFR-GITR-CD3 zeta CAR-T can target both EGFR-positive and EGFR-vIII-positive cancer cells.

The inventors have generated mesothelin-scFv-GITR-CD3 zeta-CAR-T cells against mesothelin-positive cancer cell lines such as ovarian and pancreatic cells. The inventors have demonstrated efficient expansion of the mesothelin-GITR CAR-T cells in culture. Mesothelin-GITR-CD3 zeta CAR-T cells were positive against Mesothelin-positive CAR-T cells.

The inventors have generated CD19-ScFv-GITR-CD3 zeta-CAR-T cells against CD19-positive cancer cell lines such as cervical cancer cells and hemotologic cancers. The inventors have demonstrated efficient expansion of the CD19-GITR CAR-T cells in culture. CD19-GITR-CD3 zeta CAR-T cells were positive against CD19-positive CAR-T cells.

EGFR-GITR-CD3 zeta CAR-T, mesothelin-GITR-CD3 zeta CAR-T, and CD19-GITR-CD3 zeta CAR-T can be used in combination with chemotherapy such as checkpoint inhibitors, targeted therapies, small molecule inhibitors, and antibodies.

Third generation CAR or other co-stimulatory signaling domains can be used with EGFR-GITR-CD3 zeta CAR, mesothelin-GITR-CD3 zeta CAR, and CD19-GITR-CD3 zeta CAR.

Combination of EGFR-GITR-CD3 zeta CAR-T, mesothelin-GITR-CD3 zeta CAR-T, or CD19-GITR-CD3 zeta CAR-T with CAR-T targeting other tumor antigens or tumor microenvironment (VEGFR-1-3) can be used to enhance activity of a monotherapy.

Bi-scFv-GITR CAR can be used to enhance activity of a single antibody scFv-GITR CAR, scFv-mesothelin CAR or scFv-CD19 CAR.

The following examples further illustrate the present invention. These examples are intended merely to be illustrative of the present invention and are not to be construed as being limiting.

Examples

The inventors generated EGFR, Mesothelin (Meso), CD19 CAR constructs inside lentiviral vector cloned into Xba I and EcoR I sites of lentiviral vector. pCD510-FMC63-28z lentiviral CAR construct containing the CD8 signal peptide-EGFRscFv (or Meso scFv, or CD19 scFv)-CD8 hinge-CD28 transmembrane intracellular domain-GITR domain-CD3 zeta insert—between the Xba I and EcoRI cloning sites.

The lentiviruses were generated in 293T cells and titer was established by RT-PCR. Then an equal dose of lentiviruses was used for transduction of T cells, as described in Examples Section. We used CAR lentiviruses to transduce T cells and also used control non-transduced T cells to test cytotoxic activities of CAR-T cells against EGFR, mesothelin, or CD19-positive cell lines.

Example 1. Cell Lines

A1847, SKOV-3, ovarian cells and BxPC3 pancreatic cancer cells were cultured in DMEM (GE Healthcare, Chicago, Ill.) containing 10% FBS (AmCell, Mountain View, Calif.). Human peripheral blood mononuclear cells (PBMC) were isolated by density sedimentation over Ficoll-Paque (GE Healthcare). HEK293FT cells were a gift from AlStem (Richmond, Calif.) and were cultured in DMEM containing 10% FBS. All cell lines were authenticated by flow cytometry in our laboratory, using cell-specific surface markers.

Example 2. EGFR, Mesothelin, CD19 CAR Constructs

The ScFvs of Mesothelin P4 human antibody (Lanitis, et al. (2012), *Mol Ther* 20, 633-643), EGFR C10 human antibody ((Liu et al (2015) Cancer Res 75, 3596-3607), or mouse CD19 FMC063 (Kochenderfer et al, 2009, *J Immunother* 32, 689-702. [13] were inserted into a second-generation CAR cassette flanked by Nhe I and Xho I restriction sites between a signaling peptide from human CD8, and a hinge region from CD8 alpha, then followed by transmembrane domain and costimulatory domains from (i) CD28, or (ii) GITR domain, and the CD3 zeta activation domain as shown in FIG. 3. DNAs encoding the CARs were synthesized and subcloned into a third-generation lentiviral vector, Lenti CMV-MCS-EF1a-puro by Syno Biological (Beijing, China). All CAR lentiviral constructs were sequenced in both directions to confirm CAR sequence and used for lentivirus production.

Example 3. Generation of CAR-Encoding Lentivirus

Ten million growth-arrested HEK293FT cells (Thermo Fisher) were seeded into T75 flasks and cultured overnight, then transfected with the pPACKH1 Lentivector Packaging mix (System Biosciences, Palo Alto, Calif.) and 10 μg of each lentiviral vector using the CalPhos Transfection Kit (Takara, Mountain View, Calif.). The next day the medium was replaced with a fresh medium, and 48 h later the lentivirus-containing medium was collected. The medium was cleared of cell debris by centrifugation at 2100 g for 30 min. The virus particles were collected by centrifugation at 112,000 g for 100 min, suspended in AIM V medium, aliquoted and frozen at −80° C. The titers of the virus (expressed in pfu/ml) were determined by quantitative RT-PCR using the Lenti-X qRT-PCR kit (Takara) according to the manufacturer's protocol and the 7900HT thermal cycler (Thermo Fisher).

Example 4. Generation and Expansion of CAR-T Cells

PBMCs were suspended at $1\times10^6$ cells/ml in AIM V-AlbuMAX medium (Thermo Fisher) containing 10% FBS and 300 U/ml IL-2 (Thermo Fisher), mixed with an equal number (1:1 ratio) of CD3/CD28 Dynabeads (Thermo Fisher), and cultured in non-treated 24-well plates (0.5 ml per well). At 24 and 48 hours, lentivirus was added to the cultures at a multiplicity of infection (MOI) of 5, along with 1 μl of TransPlus transduction enhancer (AlStem). As the T cells proliferated over the next two weeks, the cells were counted every 2-3 days and fresh medium with 300 U/ml IL-2 was added to the cultures to maintain the cell density at $1-3\times10^6$ cells/ml.

Example 5. Flow Cytometry

To measure CAR expression, 0.5 million cells were suspended in 100 μl of buffer (PBS containing 0.5% BSA) and incubated on ice with 1 μl of human serum (Jackson Immunoresearch, West Grove, Pa.) for 10 min. Then 1 μl of allophycocyanin (APC)-labeled anti-CD3 (eBioscience, San Diego, Calif.), 2 μl of 7-aminoactinomycin D (7-AAD, BioLegend, San Diego, Calif.), and 2 μl of biotin-labeled polyclonal goat anti-human-F(ab)$_2$ antibodies (Life Technologies) that detect EGFR scFv, Meso scFv, or CD19 scFv, or biotin-labeled normal polyclonal goat IgG antibodies (Life Technologies) were to detect CAR expression. The cells were rinsed with 3 ml of buffer, then suspended in buffer and acquired on a FACSCalibur (BD Biosciences). Cells were analyzed first for light scatter versus 7-AAD staining, then the 7-AAD⁻ live gated cells were plotted for CD3 staining versus F(as)$_2$ staining or isotype control staining.

Example 6. Real-Time Cytotoxicity Assay (RTCA)

Adherent target cells were seeded into 96-well E-plates (Acea Biosciences, San Diego, Calif.) at $1\times10^4$ cells per well and monitored in culture overnight with the impedance-based real-time cell analysis (RTCA) iCELLigence system (Acea Biosciences). The next day, the medium was removed and replaced with AIM V-AlbuMAX medium containing 10% FBS$\pm 1\times10^5$ effector cells (CAR-T cells or non-transduced T cells), in triplicate. The cells in the E-plates were monitored for another 2 days with the RTCA system, and impedance was plotted over time. Cytolysis was calculated as (impedance of target cells without effector cells—impedance of target cells with effector cells)×100/impedance of target cells without effector cells.

Example 7. Cytokine Secretion Assay

The target cells were cultured with the effector cells (CAR-T cells or non-transduced T cells) at a 1:1 ratio ($1\times10^4$ cells each) in U-bottom 96-well plates with 200 μl of of AIM V-AlbuMAX medium containing 10% FBS, in triplicate. After 16 h the top 150 μl of medium was transferred to V-bottom 96-well plates and centrifuged at 300 g for 5 min to pellet any residual cells. The top 120 μl of supernatant was transferred to a new 96-well plate and analyzed by ELISA for human IFN-gamma and IL-2 levels using kits from Thermo Fisher according to the manufacturer's protocol.

Example 8. EGFR-GITR-CD3 Zeta CAR Sequences

The CAR construct of this example: Human CD8 signaling peptide, human EGFR scFv derived from C10 low affinity EGFR antibody [5, 8] ($V_H$-Linker-$V_L$), CD8 hinge, CD28 transmembrane, co-stimulatory domain (GITR), CD3 zeta activation domain (see FIG. 3). C10 EGFR antibody has dissociation constant $K_D$ of 265 nM for A431 cells.

The nucleotide sequence of lentiviral vector with EGFR-GITR-CD3 zeta CAR (FIG. 3) inside EcoR1 and XhoI site is shown in SEQ ID NO: 1. The EGFR scFv is flanked with NheI and XhoI sites and can be substituted by other scFv such as MESO scFv or CD19 scFv.

SEQ ID NO: 1:
tctagagccgccaccATGGCCTTACCAGTGACCGCCTTGCTCCTGCCGCT

GGCCTTGCTGCTCCACGCCGCCAGGCCGgctagc gaagtgcagctggtgcagagcggcgcggaagtgaaaaaaccgggcagcag cgtgaaagtgagctgcaaagcgagcggcggcacctttagcagctatgcga ttagctgggtgcgccaggcgccgggccagggcctggaatggatgggcggc attattccgatttttggcaccgcgaactatgcgcagaaatttcagggccg cgtgaccattaccgcggatgaaagcaccagcaccgcgtatatggaactga gcagcctgcgcagcgaagataccgcggtgtattattgcgcgcgcgaagaa ggcccgtattgcagcagcaccagctgctatggcgcgtttgatatttgggg ccagggcaccctggtgaccgtgagcagc

GGTGGCGGTGGTTCT GGTGGCGGTGGTTCT GGTGGCGGTGGTTCT cagagcgtgctgacccaggatccggcggtgagcgtggcgctgggccagac cgtgaaaattacctgccagggcgatagcctgcgcagctattttgcgagct ggtatcagcagaaacggggccaggcgccgaccctggtgatgtatgcgcgc aacgatcgcccggcgggcgtgccggatcgctttagcggcagcaaaagcgg -continued
```
caccagcgcgagcctggcgattagcggcctgcagagcgaagatgaagcgg attattattgcgcggcgtgggatgatagcctgaacggctatctgtttggc gcgggcaccaaactgaccgtgctg ctcgagAAGCCCACCACGACGCCAGCGCCGCGACCACCAACACCGGCGCC

CACCATCGCGTCGCAGCCCCTGTCCCTGCGCCCAGAGGCGAGCCGGCCAG

CGGCGGGGGGCGCAGTGCACACGAGGGGGCTGGACTTCGCCAGTGATaag cccttttgggtgctggtggtggttggtggagtcctggcttgctatagctt gctagtaacagtggcctttattattttctgggtg

CAGCTTGGACTGCACATCTGGCAGCTGAGGAGTCAGTGCATGTGGCCCCG

AGAGACCCAGCTGCTGGAGGTGCCGCCGTCGACCGAAGACGCCAGAA

GCTGCCAGTTCCCCGAGGAAGAGCGGGGCGAGCGATCGGCAGAGGAGAAG

GGGCGGCTGGGAGACCTGTGGGTG

AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGCAG

AGAAGGAAGAACCCTCAGGAAGGCCTGTACAATGAACTGCAGAAAGATAA

GATGGCGGAGGCCTACAGTGAGATTGGGATGAAAGGCGAGCGCCGGAGGG

GCAAGGGGCACGATGGCCTTTACCAGGGTCTCAGTACAGCCACCAAGGAC

ACCTACGACGCCCTTCACATGCAGGCCCTGCCCCCTCGCTAAtaggaatt c
```

SEQ ID NO: 2 below is the amino acid sequence of
SEQ ID NO: 1.

M A L P V T A L L L P L A L L L H A A R P A S <u>E V
Q L V Q S G A E V K K P G S S V K V S C K A S G G
T F S S Y A I S W V R Q A P G Q G L E W M G G I I
P I F G T A N Y A Q K F Q G R V T I T A D E S T S
T A Y M E L S S L R S E D T A V Y Y C A R E E G P
Y C S S T S C Y G A F D I W G Q G T L V T V S S G
G G G S G G G G S G G G G S Q S V L T Q D P A V S
V A L G Q T V K I T C Q G D S L R S Y F A S W Y Q
Q K P G Q A P T L V M Y A R N D R P A G V P D R F
S G S K S G T S A S L A I S G L Q S E D E A D Y Y
C A A W D D S L N G Y L F G A G T K L T V L L</u> E K
P T T <u>T</u> P A P R P P T P A P T I A S Q P L S L R P
E A S R P A A G G A V H T R G L D F A S D K P F W
V L V V V G G V L A C Y S L L V T V A F I I F W V
Q L G L H I W Q L R S Q C M W P R E T Q L L L E V
P P S T E D A R S C Q F P E E E R G E R S A E E K
G R L G D L W V <u>R V K F S R S A D A P A Y Q Q G Q
N Q L Y N E L N L G R R E E Y D V L D K R R G R D</u>

-continued
<u>P E M G G K P Q R R K N P Q E G L Y N E L Q K D K
M A E A Y S E I G M K G E R R R G K G H D G L Y Q
G L S T A T K D T Y D A L H M Q A L P P R</u>

The scheme of EGFR-GITR CAR construct is shown below, which shows the sub-domain nucleotide sequences and amino acid sequences of SEQ ID NOs: 1 and 2, respectively.

<huCD8 signal peptide>
(SEQ ID NO: 3)
ATGGCCTTACCAGTGACCGCCTTGCTCCTGCCGCTGGCCTTGCTGCTCCA

CGCCGCCAGGCCG (SEQ ID NO: 4)
M A L P V T A L L L P L A L L L H A A R P

<NheI restriction site>
GCTAGC
Amino-acids: AS

<EGFR scFV>
Nucleotide sequence:
SEQ ID NO: 5
gaagtgcagctggtgcagagcggcgcggaagtgaaaaaaccgggcagcag cgtgaaagtgagctgcaaagcgagcggcggcacctttagcagctatgcga ttagctgggtgcgccaggcgccgggccagggcctggaatggatgggcggc attattccgattttggcaccgcgaactatgcgcagaaatttcagggccg cgtgaccattaccgcggatgaaagcaccagcaccgcgtatatggaactga gcagcctgcgcagcgaagataccgcggtgtattattgcgcgcgcgaagaa ggcccgtattgcagcagcaccagctgctatggcgcgtttgatatttgggg ccagggcaccctggtgaccgtgagcagc

GGTGGCGGTGGTTCT GGTGGCGGTGGTTCT GGTGGCGGTGGTTCT cagagcgtgctgacccaggatccggcggtgagcgtggcgctgggccagac cgtgaaaattacctgccagggcgatagcctgcgcagctattttgcgagct ggtatcagcagaaaccgggccaggcgccgaccctggtgatgtatgcgcgc aacgatcgcccggcgggcgtgccggatcgctttagcggcagcaaaagcgg caccagcgcgagcctggcgattagcggcctgcagagcgaagatgaagcgg attattattgcgcggcgtgggatgatagcctgaacggctatctgtttggc gcgggcaccaaactgaccgtgctg Amino-acid sequence:, SEQ ID NO: 6 which is the
underlined sequence in SEQ ID NO: 2

<u>E V Q L V Q S G A E V K K P G S S V K V S C K A S
G G T F S S Y A I S W V R Q A P G Q G L E W M G G
I I P I F G T A N Y A Q K F Q G R V T I T A D E S
T S T A Y M E L S S L R S E D T A V Y Y C A R E E
G P Y C S S T S C Y G A F D I W G Q G T L V T V S
S G G G G S G G G G S G G G G S Q S V L T Q D P A
V S V A L G Q T V K I T C Q G D S L R S Y F A S W
Y Q Q K P G Q A P T L V M Y A R N D R P A G V P D</u>

-continued

R F S G S K S G T S A S L A I S G L Q S E D E A D

Y Y C A A W D D S L N G Y L F G A G T K L T V L

<XhoI restriction site>
CTCGAG
Amino-acids: LE

<CD8 hinge>
(SEQ ID NO: 7)
AAGCCCACCACGACGCCAGCGCCGCGACCACCAACACCGGCGCCCACCAT

CGCGTCGCAGCCCCTGTCCCTGCGCCCAGAGGCGAGCCGGCCAGCGGCGG

GGGGCGCAGTGCACACGAGGGGGCTGGACTTCGCCAGTGATaagccc

Amino-acid sequence:, SEQ ID NO: 8 which is the
larger font, bold sequence in SEQ ID NO: 2
K P T T T P A P R P P T P A P T I A S Q P L S L R

P E A S R P A A G G A V H T R G L D F A S D K P

<CD28 transmembrane domain (CD28 TM)>
(SEQ ID NO: 9)
TTTTGGGTGCTGGTGGTGGTTGGTGGAGTCCTGGCTTGCTATAGCTTGCT

AGTAACAGTGGCCTTTATTATTTTCTGGGTG

Amino-acid sequence:
(SEQ ID NO: 10)
F W V L V V V G G V L A C Y S L L V T V A F I I F

W V

<GITR intracellular domain, gitr>
(SEQ ID NO: 11)
CAGCTTGGACTGCACATCTGGCAGCTGAGGAGTCAGTGCATGTGGCCCCG

AGAGACCCAGCTGCTGCTGGAGGTGCCGCCGTCGACCGAAGACGCCAGAA

GCTGCCAGTTCCCCGAGGAAGAGCGGGGCGAGCGATCGGCAGAGGAGAAG

GGGCGGCTGGGAGACCTGTGGGTG

Amino-acid sequence:, SEQ ID NO: 12 which is the
bold sequence in SEQ ID NO: 2
Q L G L H I W Q L R S Q C M W P R E T Q L L L E V

P P S T E D A R S C Q F P E E E R G E R S A E E K

G R L G D L W V

<CD3 zeta activation domain>
(SEQ ID NO: 13)
AGAGTGAAGTTCAGCAGGAGCGCAGACGCCCCCGCGTACCAGCAGGGCCA

GAACCAGCTCTATAACGAGCTCAATCTAGGACGAAGAGAGGAGTACGATG

TTTTGGACAAGAGACGTGGCCGGGACCCTGAGATGGGGGGAAAGCCGAGA

AGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCA

AGGGGCACGATGGCCTTTACCAGGGTCTCAGTACAGCCACCAAGGACACC

TACGACGCCCTTCACATGCAGGCCCTGCCCCCTCGCTAATAG

Amino-acid sequence:, SEQ ID NO: 14 which is in
italics, larger font, underlined in SEQ ID NO: 2
R V K F S R S A D A P A Y Q Q G Q N Q L Y N E L N L G R R E E Y D V L D K R R G R D P E Met G G K P

R R K N P Q E G L Y N E L Q K D K M A E A Y S E I

G M K G E R R R G K G H D G L Y Q G L S T A T K D

T Y D A L H M Q A L P P R

Example 9. The Sequence of EGFR-GITR-CD3 Zeta-CAR

This construct includes human CD8 signaling peptide, human EGFR scFv ($V_H$-Linker-$V_L$) derived from P3-5 [5, 8], CD8 hinge, CD28 transmembrane, GITR co-stimulatory domain, CD3 zeta activation domain (FIG. 3). P3-5 has $K_D$=88 nM for 431 cells. Linker is 3×(GGGGS, SEQ ID NO: 15).

The sequences are similar to those described in Example 8 except the human EGFR scFv is derived from P3-5.

$V_H$ P3-5

The underlined and bold amino-acids are different from C10 Amino-acid sequence.
(SEQ ID NO: 16)
EVQLVQSGAEVKKPGSSVKSCKASGGTFSSYAISWVRQAPGQGLEW<u>V</u>GGI IPIFGTANYAQKFQGRV<u>K</u>ITADES<u>A</u>STAYMELSSLRSEDTAVYYCAREEG

PYCSSTSCYGAFDIWGQGTLVTVSS

Reverse translate using www.bioinformatics.org/sms2/rev_trans.html to a 375 base sequence of most likely codons.
(SEQ ID NO: 17)
gaagtgcagctggtgcagagcggcgcggaagtgaaaaaaccgggcagcag cgtgaaaagctgcaaagcgagcggcggcacctttagcagctatgcgatta gctgggtgcgccaggcgccgggccagggcctggaatgggtgggcggcatt attccgatttttggcaccgcgaactatgcgcagaaatttcagggccgcgt gaaaattaccgcggatgaaagcgcgagcaccgcgtatatggaactgagca gcctgcgcagcgaagataccgcggtgtattattgcgcgcgcgaagaaggc ccgtattgcagcagcaccagctgctatggcgcgtttgatatttggggcca gggcacccctggtgaccgtgagcagc $V_L$ P3-5

The underlined amino-acids are different from C10 Amino-acid sequence.
(SEQ ID NO: 18)
QSVLTQDPAVSVALGQTVKITCQGDSLRSY<u>L</u>ASWYQQKPGQAPTLV<u>T</u>YAR

NDRPAGVPDRFSGSKSGTSASLAISGLQSEDEADYYCAAWDDSLNGYLFG

AGTKLTVL

Reverse translation of amino-acid sequence to a 324 base sequence of most likely codons.
(SEQ ID NO: 19)
cagagcgtgctgacccaggatccggcggtgagcgtggcgctgggccagac cgtgaaaattacctgccagggcgatagcctgcgcagctatctggcgagct ggtatcagcagaaacccgggccaggcgccgaccctggtgacctatgcgcgc aacgatcgcccggcgggcgtgccggatcgctttagcggcagcaaaagcgg caccagcgcgagcctggcgattagcggcctgcagagcgaagatgaagcgg attattattgcgcggcgtgggatgatagcctgaacggctatctgtttggc gcgggcaccaaactgaccgtgctg

Example 10. The Sequence of EGFR-CD28-CD3 Zeta CAR

This construct includes human CD8 signaling peptide, human EGFR scFv ($V_H$-Linker-$V_L$), CD8 hinge, CD28 transmembrane, CD28 co-stimulatory domain, CD3 zeta activation domain (see FIG. 3). Linker is 3×(GGGGS, SEQ ID NO: 15).

The sequences are similar to those described in Example 8 except CD28 is used as a co-stimulatory domain.

<CD28 co-stimulatory domain sequence>
Nucleotide sequence:
(SEQ ID NO: 20)
AGGAGTAAGAGGAGCAGGCTCCTGCACAGTGACTACATGAACATGACTCC

CCGCCGCCCCGGGCCCACCCGCAAGCATTACCAGCCCTATGCCCCACCAC

GCGACTTCGCAGCCTATCGCTCC

Amino acid sequence:
(SEQ ID NO: 21)
R S K R S R L L H S D Y M N M T P R R P G P T R K

H Y Q P Y A P P R D F A A Y R S

Example 11. EGFR-4-1BB-CD3 Zeta CAR

This construct includes human CD8 signaling peptide, human EGFR scFv (V$_H$-Linker-V$_L$), CD8 hinge, CD28 transmembrane, 4-1BB co-stimulatory domain, CD3 zeta activation domain (see FIG. 3). Linker is 3×(GGGGS, SEQ ID NO: 15).

The sequences are similar to those described in Example 8 except 4-1BB is used as a co-stimulatory domain.

4-1BB co-stimulatory domain sequence:
Nucleotide sequence:
(SEQ ID NO: 22)
AAACGGGGCAGAAAGAAACTCCTGTATATATTCAAACAACCATTTATGA

GACCAGTACAAACTACTCAAGAGGAAGATGGCTGTAGCTGCCGATTTCC

AGAAGAAGAAGAAGGAGGATGTGAACTG

Amino-acid sequence
(SEQ ID NO: 23)
K R G R K K L L Y I F K Q P F Met R P V Q T T Q E

E D G C S C R F P E E E E G G C E L

Example 12. Mesothelin-GITR-CD3 Zeta CAR Sequence

Instead of EGFR ScFV in SEQ ID NOs: 1 and 2 as shown in Example 8, mesothelin (human P4 Ab) ScFv was inserted into Xho I and Nhe I of SEQ ID NO: 1.

The Mesothelin-GITR CAR nucleotide sequence is shown in SEQ ID NO: 24 below. The first two highlighted GCTAGC and CTCGAG indicate Xho I and Nhe I sites of mesothelin insertion, respectively. The third highlighted CAGCTT indicates GITR start.

```
ATGGCCTTACCAGTGACCGCCTTGCTCCTGCCGCTGGCCTTGCTGCTCCACGCCGCC

AGGCCGGCTAGCGAAGTGCAGCTGGTGCAGAGCGGCGCGGAAGTGAAAAAACCGG

GCAGCAGCGTGAAAGTGAGCTGCAAAGCGAGCGGCGGCACCTTTAGCAGCTATGCG

ATTAGCTGGGTGCGCCAGGCGCCGGGCCAGGGCCTGGAATGGATGGGCGGCATTAT

TCCGATTTTTGGCACCGCGAACTATGCGCAGAAATTTCAGGGCCGCGTGACCATTAC

CGCGGATGAAAGCACCAGCACCGCGTATATGGAACTGAGCAGCCTGCGCAGCGAAG

ATACCGCGGTGTATTATTGCGCGCGCGAAGAAGGCCCGTATTGCAGCAGCACCAGC

TGCTATGGCGCGTTTGATATTTGGGGCCAGGGCACCCTGGTGACCGTGAGCAGCGGT

GGCGGTGGTTCTGGTGGCGGTGGTTCTGGTGGCGGTGGTTCTCAGAGCGTGCTGACC

CAGGATCCGGCGGTGAGCGTGGCGCTGGGCCAGACCGTGAAAATTACCTGCCAGGG

CGATAGCCTGCGCAGCTATTTTGCGAGCTGGTATCAGCAGAAACCGGGCCAGGCGC

CGACCCTGGTGATGTATGCGCGCAACGATCGCCCGGCGGGCGTGCCGGATCGCTTTA

GCGGCAGCAAAAGCGGCACCAGCGCGAGCCTGGCGATTAGCGGCCTGCAGAGCGA

AGATGAAGCGGATTATTATTGCGCGGCGTGGGATGATAGCCTGAACGGCTATCTGTT

TGGCGCGGGCACCAAACTGACCGTGCTGCTCGAGAAGCCCACCACGACGCCAGCGC

CGCGACCACCAACACCGGCGCCCACCATCGCGTCGCAGCCCCTGTCCCTGCGCCCAG

AGGCGAGCCGGCCAGCGGCGGGGGGCGCAGTGCACACGAGGGGGCTGGACTTCGC

CAGTGATAAGCCCTTTTGGGTGCTGGTGGTGGTTGGTGGAGTCCTGGCTTGCTATAG

CTTGCTAGTAACAGTGGCCTTTATTATTTTCTGGGTGCAGCTTGGACTGCACATCTGG

CAGCTGAGGAGTCAGTGCATGTGGCCCCGAGAGACCCAGCTGCTGCTGGAGGTGCC

GCCGTCGACCGAAGACGCCAGAAGCTGCCAGTTCCCCGAGGAAGAGCGGGGCGAG

CGATCGGCAGAGGAGAAGGGGCGGCTGGGAGACCTGTGGGTGAGAGTGAAGTTCA
```

```
GCAGGAGCGCAGACGCCCCCGCGTACCAGCAGGGCCAGAACCAGCTCTATAACGAG

CTCAATCTAGGACGAAGAGAGGAGTACGATGTTTTGGACAAGAGACGTGGCCGGGA

CCCTGAGATGGGGGGAAAGCCGCAGAGAAGGAAGAACCCTCAGGAAGGCCTGTAC

AATGAACTGCAGAAAGATAAGATGGCGGAGGCCTACAGTGAGATTGGGATGAAAG

GCGAGCGCCGGAGGGGCAAGGGGCACGATGGCCTTTACCAGGGTCTCAGTACAGCC

ACCAAGGACACCTACGACGCCCTTCACATGCAGGCCCTGCCCCCTCGCTAA

The amino acid sequence of mesothelin-GITR CAR is shown as SEQ ID NO: 25.
M A L P V T A L L L P L A L L L H A A R P A S E V Q L V Q S G A E V K K P G S S V K V S C K A S G G T F S S Y A I S W V R Q A P G Q G L E W M G G I I P I F G T A N Y A Q K F Q G R V T I T A D E S T S T A Y M E L S S L R S E D T A V Y Y C A R E E G P Y C S S T S C Y G A F D I W G Q G T L V T V S S G G G G S G G G G S G G G G S Q S V L T Q D P A V S V A L G Q T V K I T C Q G D S L R S Y F A S W Y Q Q K P G Q A P T L V M Y A R N D R P A G V P D R F S G S K S G T S A S L A I S G L Q S E D E A D Y Y C A A W D D S L N G Y L F G A G T K L T V L L E K P T T T P A P R P P T P A P T I A S Q P L S L R P E A S R P A A G G A V H T R G L D F A S D K P F W V L V V V G G V L A C Y S L L V T V A F I I F W V Q L G L H I W Q L R S Q C M W P R E T Q L L L E V P P S T E D A R S C Q F P E E E R G E R S A E E K G R L G D L W V R V K F S R S A D A P A Y Q Q G Q N Q L Y N E L N L G R R E E Y D V L D K R R G R D P E M G G K P Q R R K N P Q E G L Y N E L Q K D K M A E A Y S E I G M K G E R R R G K G H D G L Y Q G L S T A T K D T Y

D A L H M Q A L P P R
```

Example 13. CD19-GITR-CD3 Zeta CAR Sequence

Instead of EGFR ScFV shown in Example 8 in SEQ ID No 1 and 2, CD19 ScFv was inserted into Xho I and Nhe I sites in SEQ ID NO: 1.

The CD19-GITR-Zeta CAR nucleotide sequence is shown in SEQ ID NO: 26 below. The first two highlighted GCTAGC and CTCGAG indicate Xho I and Nhe I sites of CD19 ScFv insertion. The third highlighted CAGCTT indicates GITR start.

```
ATGGCCTTACCAGTGACCGCCTTGCTCCTGCCGCTGGCCTTGCTGCTCCACGCCGCC

AGGCCGgctagc gacatccagatgacacagactacatcctccctgtctgcctctctgggagacagagtcaccatcagttgcagggcaagtcaggacattagtaa atatttaaattggtatcagcagaaaccagatggaactgttaaactcctgatctaccatacatcaagattacactcaggagtcccatcaaggttca gtggcagtgggtctggaacagattattctctcaccattagcaacctggagcaagaagatattgccacttacttttgccaacagggtaatacgct tccgtacacgttcggaggggggactaagttggaaataacaggctccacctctggatccggcaagcccggatctggcgagggatccacca agggcgaggtgaaactgcaggagtcaggacctggcctggtggcgccctcacagagcctgtccgtcacatgcactgtctcaggggtctcat tacccgactatggtgtaagctggattcgccagcctccacgaaagggtctggagtggctgggagtaatatggggtagtgaaaccacatactat aattcagctctcaaatccagactgaccatcatcaaggacaactccaagagccaagttttcttaaaaatgaacagtctgcaaactgatgacaca gccatttactactgtgccaaacattattactacggtggtagctatgctatggactactggggtcaaggaacctcagtcaccgtctcctcagcgg ccgca ctcgagAAGCCCACCACGACGCCAGCGCCGCGACCACCAACACCGGCGCCCACCATCG

CGTCGCAGCCCCTGTCCCTGCGCCCAGAGGCGAGCCGGCCAGCGGCGGGGGGCGCA

GTGCACACGAGGGGGCTGGACTTCGCCAGTGATaagccctttgggtgctggtggtggttggtggagtcctg gcttgctatagcttgctagtaacagtggcctttattattttctgggtg
```

CAGCTTGGACTGCACATCTGGCAGCTGAGGAGTCAGTGCATGTGGCCCCGA

GAGACCCAGCTGCTGCTGGAGGTGCCGCCGTCGACCGAAGACGCCAGAAGCTGCCA

GTTC

CCCGAGGAAGAGCGGGGCGAGCGATCGGCAGAGGAGAAGGGGCGGCTGGGAGACC

TGTGG

GTG

AGATGAAGTTCAGCAGGAGCGCAGACGCCCCCGCGTACCAGCAGGGCCAGAACC

AGCTCTATAACGAGCTCAATCTAGGACGAAGAGAGGAGTACGATGTTTTGGACAAG

AGACGTGGCCGGGACCCTGAGATGGGGGGAAAGCCGCAGAGAAGGAAGAACCCTC

AGGAAGGCCTGTACAATGAACTGCAGAAAGATAAGATGGCGGAGGCCTACAGTGA

GATTGGGATGAAAGGCGAGCGCCGGAGGGGCAAGGGGCACGATGGCCTTTACCAG

GGTCTCAGTACAGCCACCAAGGACACCTACGACGCCCTTCACATGCAGGCCCTGCCC

CCTCGCTA

The amino acid sequence of CD19-GITR zeta CAR is shown as SEQ ID NO: 27. CD19 scFv is bolded, GITR is underlined.

M A L P V T A L L L P L A L L L H A A R P A S D I Q M T Q T T S S L S A S L G D R V T I

S C R A S Q D I S K Y L N W Y Q Q K P D G T V K L L I Y H T S R L H S G V P S R F S

G S G S G T D Y S L T I S N L E Q E D I A T Y F C Q Q G N T L P Y T F G G G T K L E

I T G S T S G S G K P G S G E G S T K G E V K L Q E S G P G L V A P S Q S L S V T C

T V S G V S L P D Y G V S W I R Q P P R K G L E W L G V I W G S E T T Y Y N S A L

K S R L T I I K D N S K S Q V F L K M N S L Q T D D T A I Y Y C A K H Y Y Y G G S

Y A M D Y W G Q G T S V T V S S A A A L E K P T T T P A P R P P T P A P T I A S Q P L

S L R P E A S R P A A G G A V H T R G L D F A S D K P F W V L V V V G G V L A C Y S

L L V T V A F I I F W V Q L G L H I W <u>Q L R S Q C M W P R E T Q L L L E V P P S T E D</u>

<u>A R S C Q F P E E E R G E R S A E E K G R L G D L W V</u> R V K F S R S A D A P A Y Q Q

G Q N Q L Y N E L N L G R R E E Y D V L D K R R G R D P E M G G K P Q R R K N P Q E

G L Y N E L Q K D K M A E A Y S E I G M K G E R R R G K G H D G L Y Q G L S T A T K

D T Y D A L H M Q A L P P R

We also used CD19-Flag ScFv and GM-CSF signaling peptide instead of CD8 signaling peptide to generate CD19-Flag-GITR-CD3 zeta CAR, the activity of this CAR was similar to the above CD19-GITR-CD3 zeta construct.

We also tested CD19-GITR-CD3 zeta with CD8 transmembrane domain (<u>IYIWAPLAGTCGVLLLSLVITLYC</u>, SEQ ID NO: 28)

instead of CD28 trans-membrane domain and both constructs (see FIG. 3) had similar activities.

The nucleotide and amino acids sequences of CD19-GITR-CD3 zeta with CD8 transmembrane domain is shown below.

(SEQ ID NO: 29)

ATGGCCTTACCAGTGACCGCCTTGCTCCTGCCGCTGGCCTTGCTGCTCCA

CGCCGCCAGGCCGGACATCCAGATGACACAGACTACATCCTCCCTGTCT

GCCTCTCTGGGAGACAGAGTCACCATCAGTTGCAGGGCAAGTCAGGAC

ATTAGTAAATATTTAAATTGGTATCAGCAGAAACCAGATGGAACTGTTA

AACTCCTGATCTACCATACATCAAGATTACACTCAGGAGTCCCATCAAG

GTTCAGTGGCAGTGGGTCTGGAACAGATTATTCTCTCACCATTAGCAAC

CTGGAGCAAGAAGATATTGCCACTTACTTTTGCCAACAGGGTAATACGC

TTCCGTACACGTTCGGAGGGGGGACTAAGTTGGAAATAACAGGTGGCG

GTGGCAGCGGCGGTGGTGGTTCCGGAGGCGGCGGTTCTGAGGTGAAAC

TGCAGGAGTCAGGACCTGGCCTGGTGGCGCCCTCACAGAGCCTGTCCGT

CACATGCACTGTCTCAGGGGTCTCATTACCCGACTATGGTGTAAGCTGG

ATTCGCCAGCCTCCACGAAAGGGTCTGGAGTGGCTGGGAGTAATATGG

GGTAGTGAAACCACATACTATAATTCAGCTCTCAAATCCAGACTGACCA

```
TCATCAAGGACAACTCCAAGAGCCAAGTTTTCTTAAAAATGAACAGTCT

GCAAACTGATGACACAGCCATTTACTACTGTGCCAAACATTATTACTAC

GGTGGTAGCTATGCTATGGACTACTGGGGTCAAGGAACCTCAGTCACC

GTCTCCTCAACCACGACGCCAGCGCCGCGACCACCAACACCGGCGCCCA

CCATCGCGTCGCAGCCCCTGTCCTGCGCCCAGAGGCGTGCCGGCCAG

CGGCGGGGGCGCAGTGCACACGAGGGGGCTGGACTTCGCCTGTGAT

ATCTACATCTGGGCGCCCCTGGCCGGGACTTGTGG

GGTCCTTCTCCTGTCACTGGTTATCACCCTTTACTGC

CAGCTTGGACTGCACATCTGGCAGCTGAGGAGTCAGTGCATGTGGCCC

CGAGAGACCCAGCTGCTGCTGGAGGTGCCGCCGTCGACCGAAGACGCC

AGAAGCTGCCAGTTCCCCGAGGAAGAGCGGGGCGAGCGATCGGCAGAG

GAGAAGGGGCGGCTGGGAGACCTGTGGGTGAGAGTGAAGTTCAGCAGG

AGCGCAGACGCCCCCGCGTACAAGCAGGGCCAGAACCAGCTCTATAAC

GAGCTCAATCTAGGACGAAGAGAGGAGTACGATGTTTTGGACAAGAGA

CGTGGCCGGGACCCTGAGATGGGGGGAAAGCCGAGAAGGAAGAACCCT

CAGGAAGGCCTGTACAATGAACTGCAGAAAGATAAGATGGCGGAGGCC

TACAGTGAGATTGGGATGAAAGGCGAGCGCCGGAGGGGCAAGGGGCAC

GATGGCCTTTACCAGGGTCTCAGTACAGCCACCAAGGACACCTACGAC

GCCCTTCACATGCAGGCCCTGCCCCCTCGCTAA
```

The amino-acid sequence of CD19-GITR-CD3 zeta CAR with CD8 trans-membrane domain is shown below, CD8 transmembrane domain is underlined, GITR domain is shown in bold.

(SEQ ID NO: 30)
M A L P V T A L L L P L A L L L H A A R P D I Q M
T Q T T S S L S A S L G D R V T I S C R A S Q D I
S K Y L N W Y Q Q K P D G T V K L L I Y H T S R L
H S G V P S R F S G S G S G T D Y S L T I S N L E
Q E D I A T Y F C Q Q G N T L P Y T F G G G T K L
E I T G G G S G G G G S G G G G S E V K L Q E S
G P G L V A P S Q S L S V T C T V S G V S L P D Y
G V S W I R Q P P R K G L E W L G V I W G S E T T
Y Y N S A L K S R L T I I K D N S K S Q V F L K M
N S L Q T D D T A I Y Y C A K H Y Y Y G G S Y A M
D Y W G Q G T S V T V S S T T T P A P R P P T P A
P T I A S Q P L S L R P E A C R P A A G G A V H T
R G L D F A C D <u>I Y I W A P L A G T C G V L L L S
L V I T L Y C</u> **Q L G L H I W Q L R S Q C M W P R E
T Q L L L E V P P S T E D A R S C Q F P E E E R G
E R S A E E K G R L G D L W V R V K F S R S A D A
P A Y K Q G Q N Q L Y N E L N L G R R E E Y D V L
D K R R G R D P E Met G G K P R R K N P Q E G L Y
N E L Q K D K M A E A Y S E I G M K G E R R R G K
G H D G L Y Q G L S T A T K D T Y D A L H M Q A L
P P R**

Figure 4:
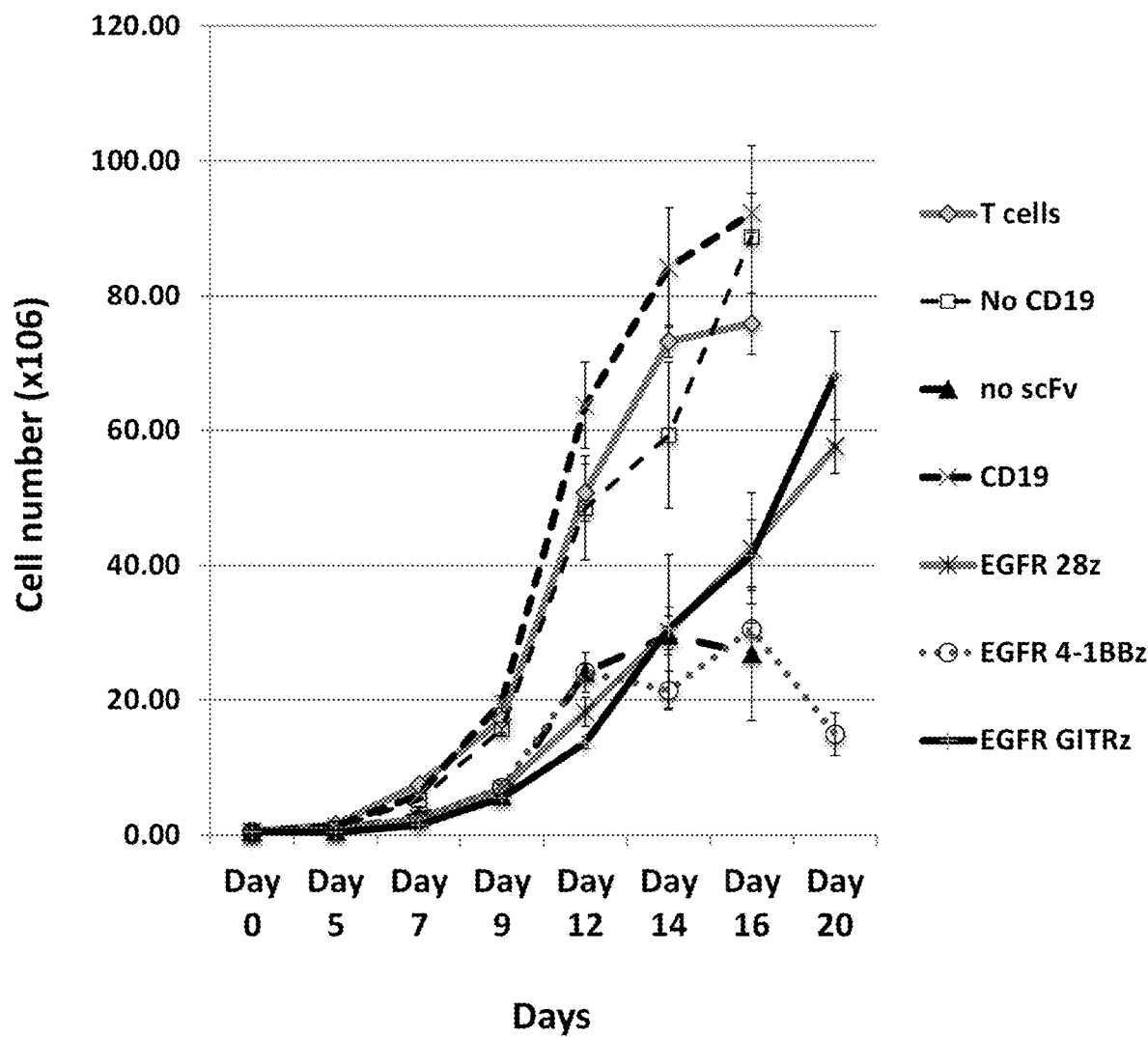
FIG. 4. Expansion of EGFR-GITR-CD3 zeta CAR-T cells in vitro.
Figure 5A:
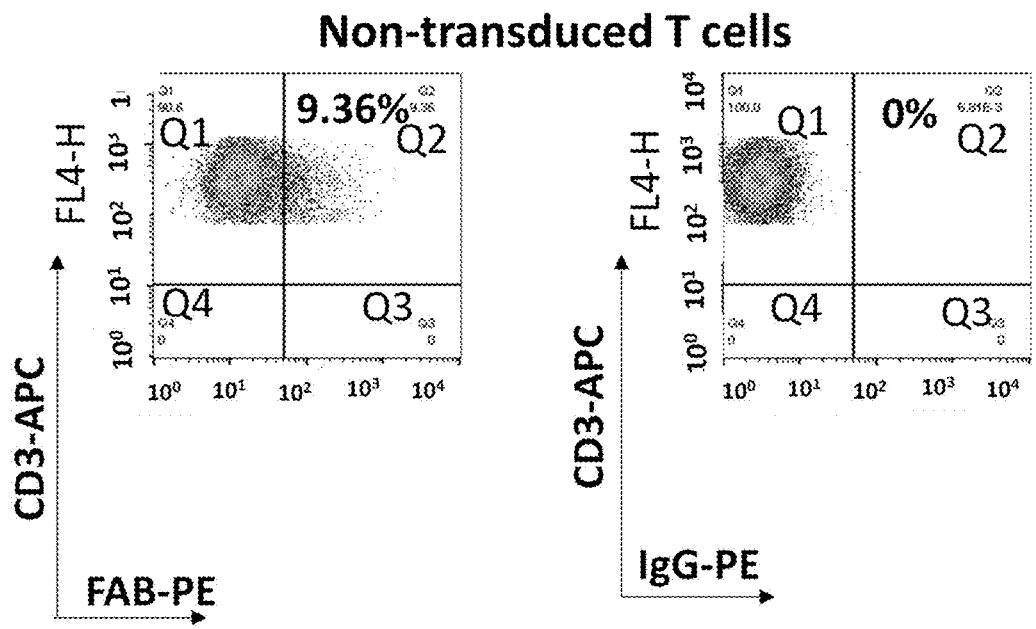
FIG. 5A-5D. FAB staining demonstrates expression of EGFR scFv in transduced T cells.
Figure 5B:
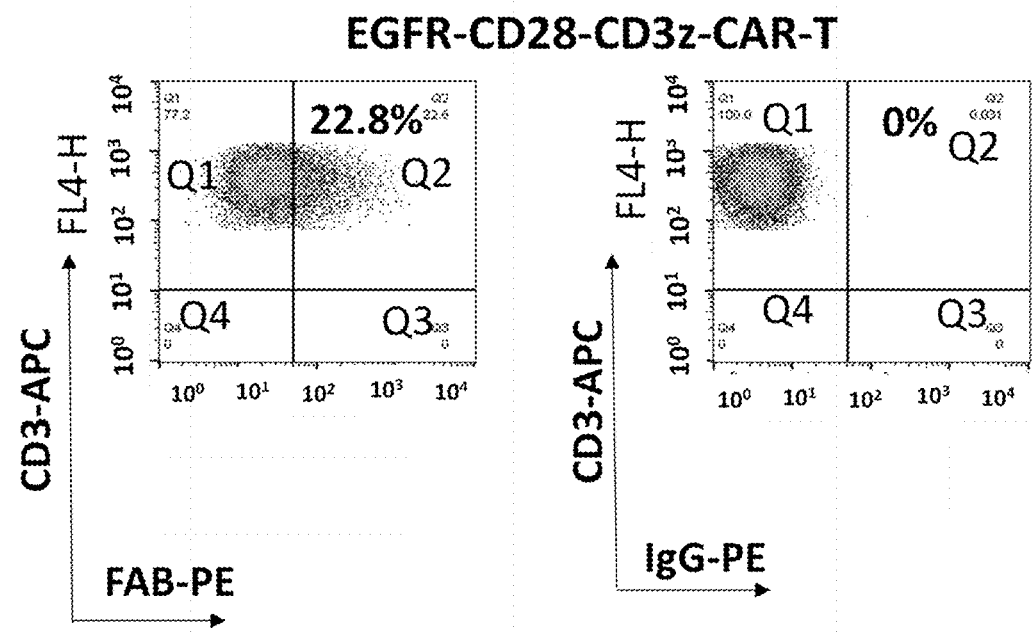
Figure 5C:
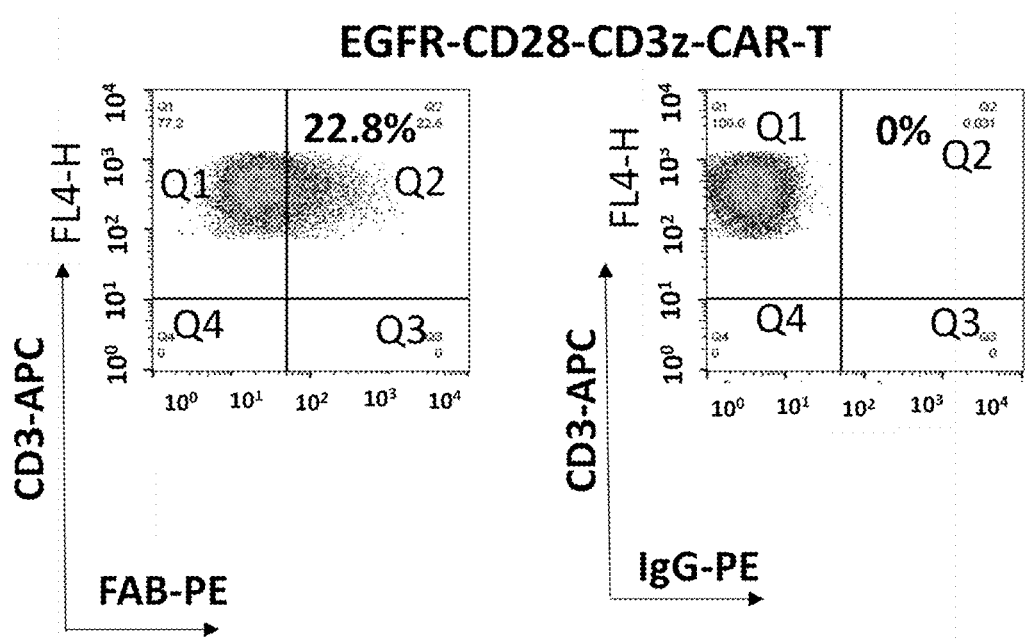
Figure 5D:
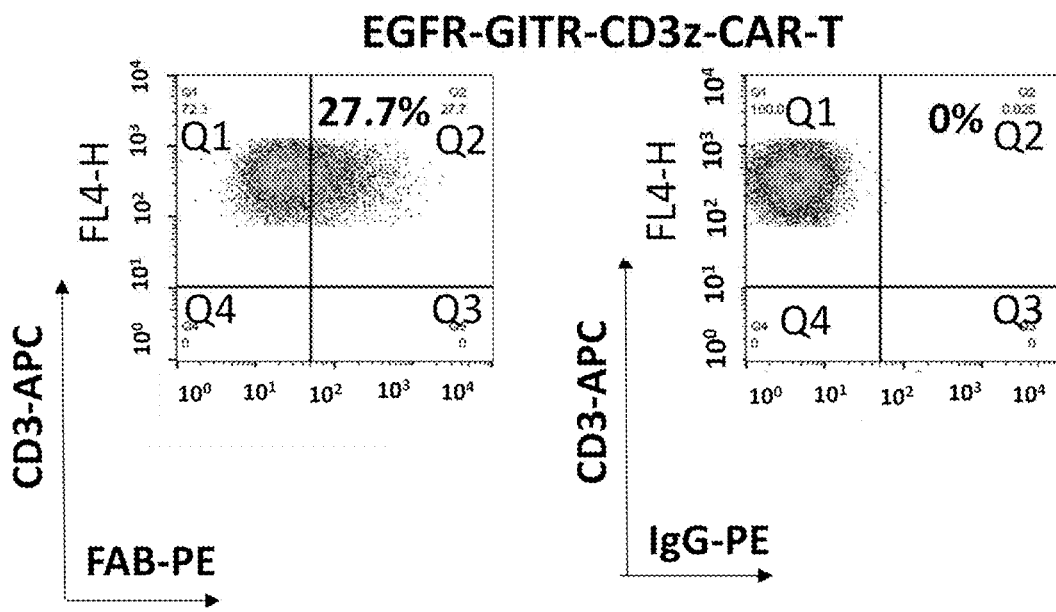

Example 14. The EGFR-GITR-CD3 Zeta CAR-T Cells Demonstrate Efficient Expansion in Culture The EGFR-GITR CAR-T cells were effectively expanded in vitro (FIG. 4). EGFR-GITR CAR-T cells were expanded more than 60-fold during 20 days in culture. The EGFR-4-1BB-CD3z-CAR-T cells slowed their growth after 16 days. The CD19-CD28-CD3 zeta CAR-T and Non-CD19-CAR-T cells and non-transduced T cells were also effectively expanded in vitro.

The results in FIG. 4 show that EGFR-GITR-CD3 zeta CAR cells expanded better than EGFR 4-1BB-CD3 zeta and EGFR 28-CD3 zeta CAR-T cells.

Example 15. Transduction of T Cells with EGFR-CAR Lentiviral Constructs Demonstrates Expression of EGFR ScFv To detect transduction the expression of human scFv from C10 EGFR antibody, CAR-T cells were stained with anti-human FAB antibody. In FIGS. 5A-5D, Fab staining demonstrates the expression of EGFR scFv in transduced T cells. Fab staining with anti-human Fab antibody in EGFR-CAR-T cells was higher than that in non-transduced T cells.

The results in FIG. 5 show efficient transduction with lentiviral CAR. The expression of EGFR scFv was 22-32% higher than that in control non-transduced cells (9.3%).

Figure 6A:
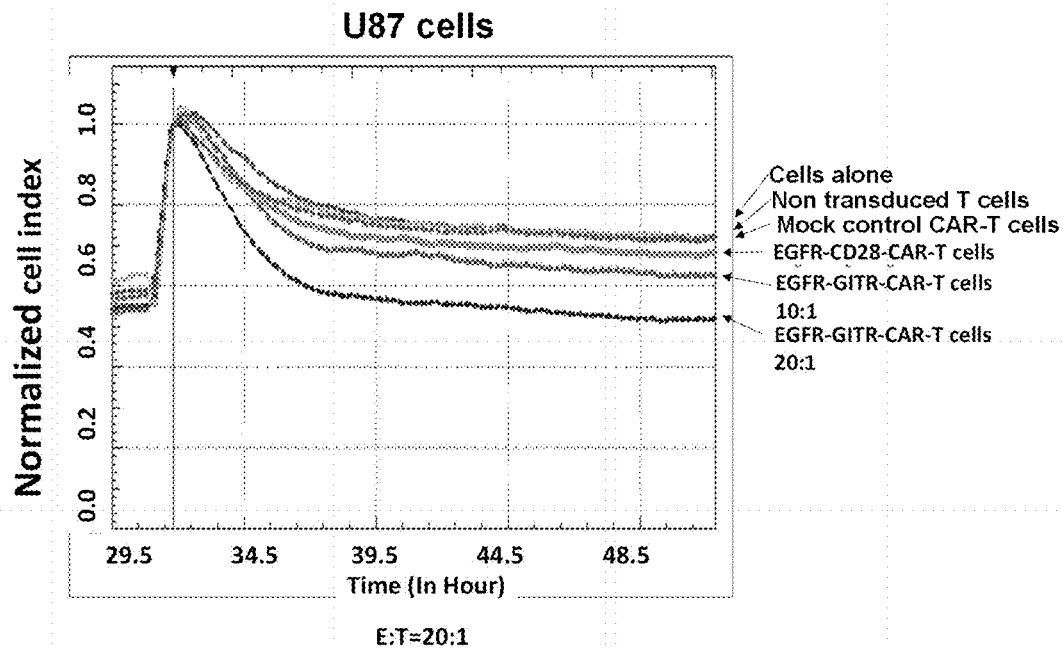
FIGS. 6A-6E. EGFR-GITR-CD3 zeta CAR-T cells were highly cytotoxic against EGFR-positive cancer cells but were not against EGFR-negative cancer cells.

Example 16. EGFR-GITR-CD3 Zeta CAR Expressed High Cytotoxic Activity Against EGFR-Positive Cancer Cells and had and No Cytotoxic Activity Against EGFR-Negative Cancer Cells The real-time cytotoxicity assay demonstrates high cytotoxic activity of EGFR-GITR-CD3 zeta-CAR cells against EGFR-positive cancer cells (FIG. 6). The cytotoxic activity of EGFR-CAR was cancer-type dependent. For example, in U87 glioblastoma cells, EGFR-GITR-CD3z-CAR-T cells had better cytotoxic activity than EGFR-CD28-CD3 zeta-CAR-T cells (FIG. 6A). The EGFR-GITR-CD3 zeta CAR-T activity was dose dependent; the activity increased at 20:1 compared to 10:1 ratio.

Figure 6B:
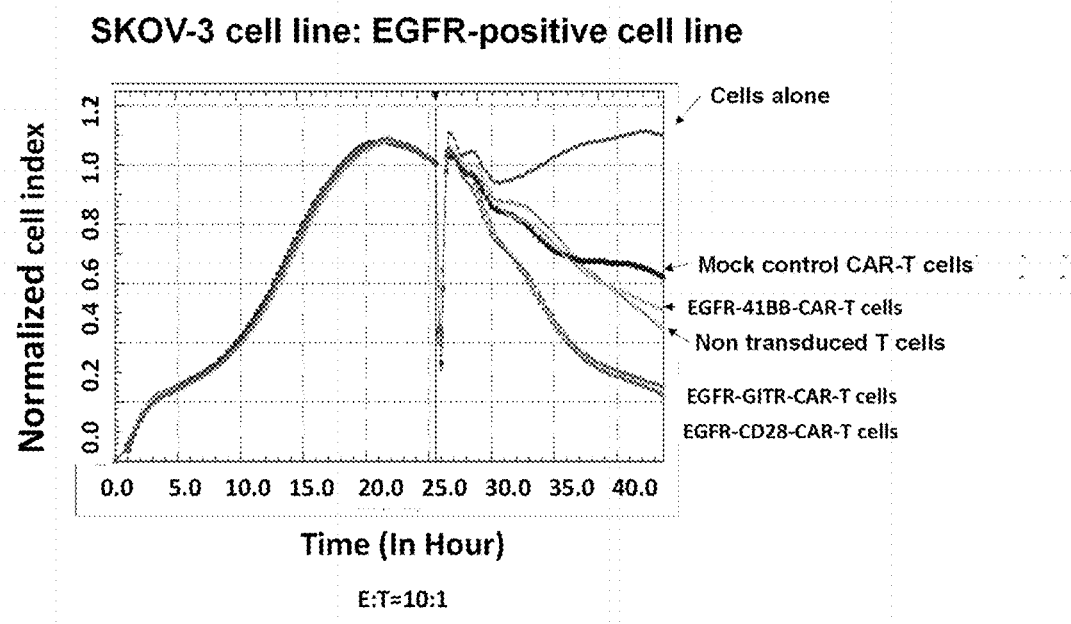

In SKOV-3 ovarian cancer cells, activities of EGFR-GITR-CD3 zeta CAR-T and EGFR-CD28-CD3 zeta CAR-T cells were the same, but higher than the activities of EGFR-4-1BB-CD3 zeta and Mock-control CAR-T cells (FIG. 6B). GITR and CD28 co-stimulatory domains had higher cytotoxic activity than 4-1BB-containing CAR-T cells in SKOV-3 ovarian cancer cells (FIG. 6B).

Figure 6C:
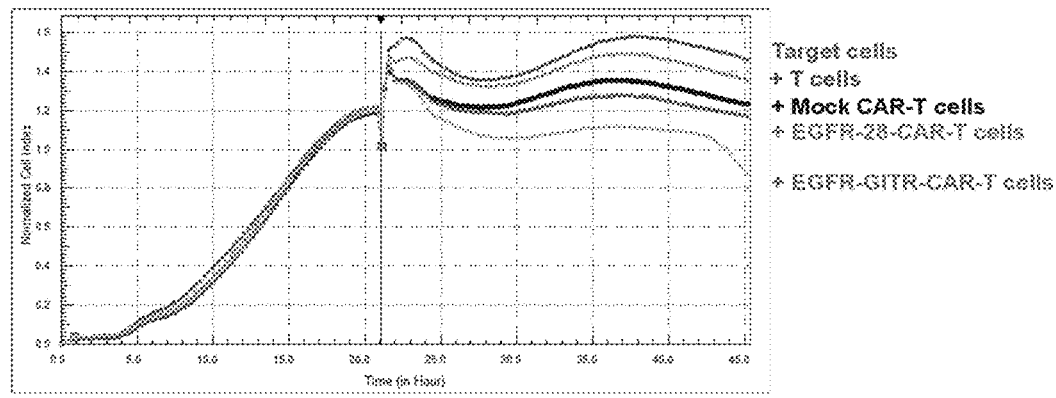

In another ovarian cancer cell line, A1847, EGFR-GITR-CD3 zeta activity was better than EGFR-CD28-CD3 zeta at 30:1 E:T (Effector: target cell ratio) (FIG. 6C).

Figure 6D:
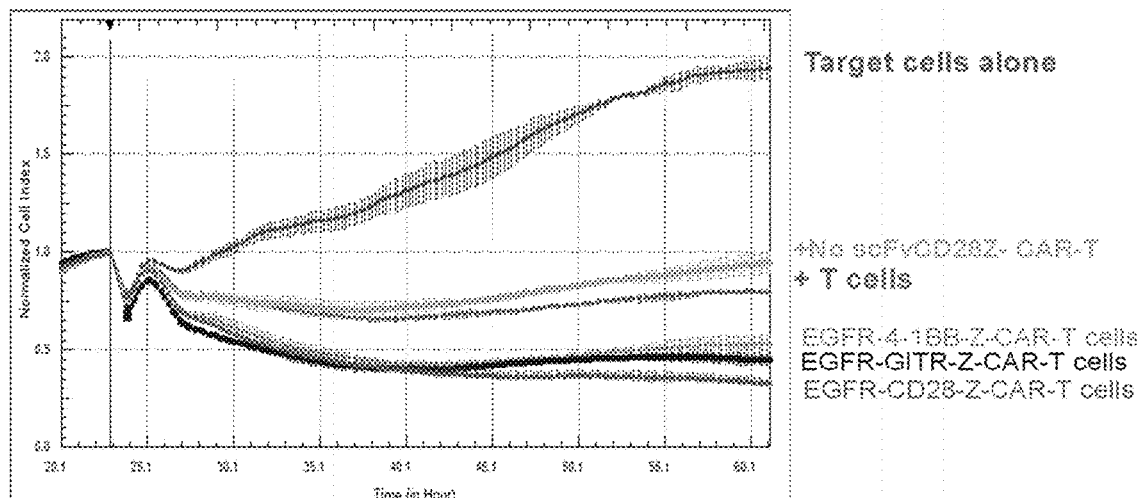
Figure 6E:
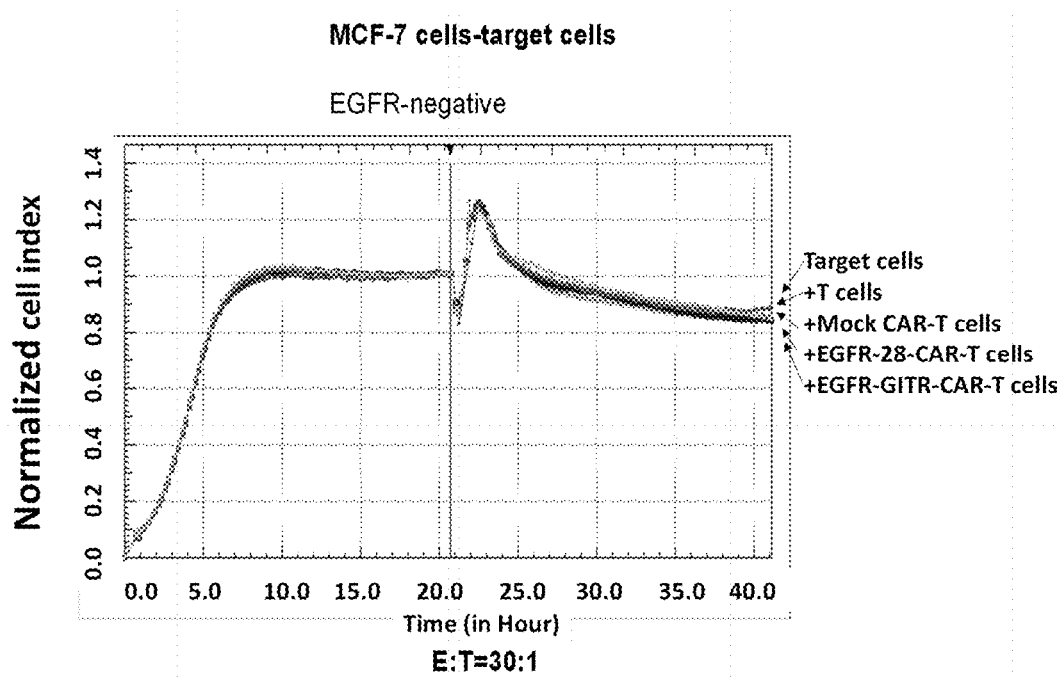

In pancreatic cancer cells BxPC3, cytotoxic activity of EGFR-CD28-CD3 zeta was higher than EGFR-GITR-CD3 zeta and EGFR-41BB-CD3 zeta (FIG. 6D). There was no cytotoxic activity in EGFR-negative cells, MCF-7 cells (FIG. 6E).

Example 17. Mesothelin-GITR-CD3 Zeta CAR Expressed High Cytotoxic Activity Against Mesothelin-Positive Cancer Cells We generated mesothelin-GITR-CD3 zeta CAR-T cells with mesothelin-GITR-CD3 zeta CAR constructs (FIG. 3) and tested their cytolytic activity in on A1847, SKOV-3 ovarian cancer and BxPC3 pancreatic cancer cells.

Lentiviral vectors with CMV promoters were used for generation of mesothelin-GITR-CD3 zeta and mesothelin-CD28-CD3 zeta (2nd generation) CAR-T cells. Lentiviral vector with EF1 promoter was used for generation of mesothelin-28-41BB-CD3 (3rd generation) CAR-T cells. Mesothelin-28-CD3 zeta CAR T cells are labelled as Meso-28-CAR-T 2nd cells. Mesothelin-GITR-CD3 zeta CAR T cells are labeled as Meso-GITR CAR-T cells. Mesothelin-28-4-1BB-CD3 zeta CAR T cells are labeled as Meso-28-CAR-T cells 3 d generation.

Figure 7:
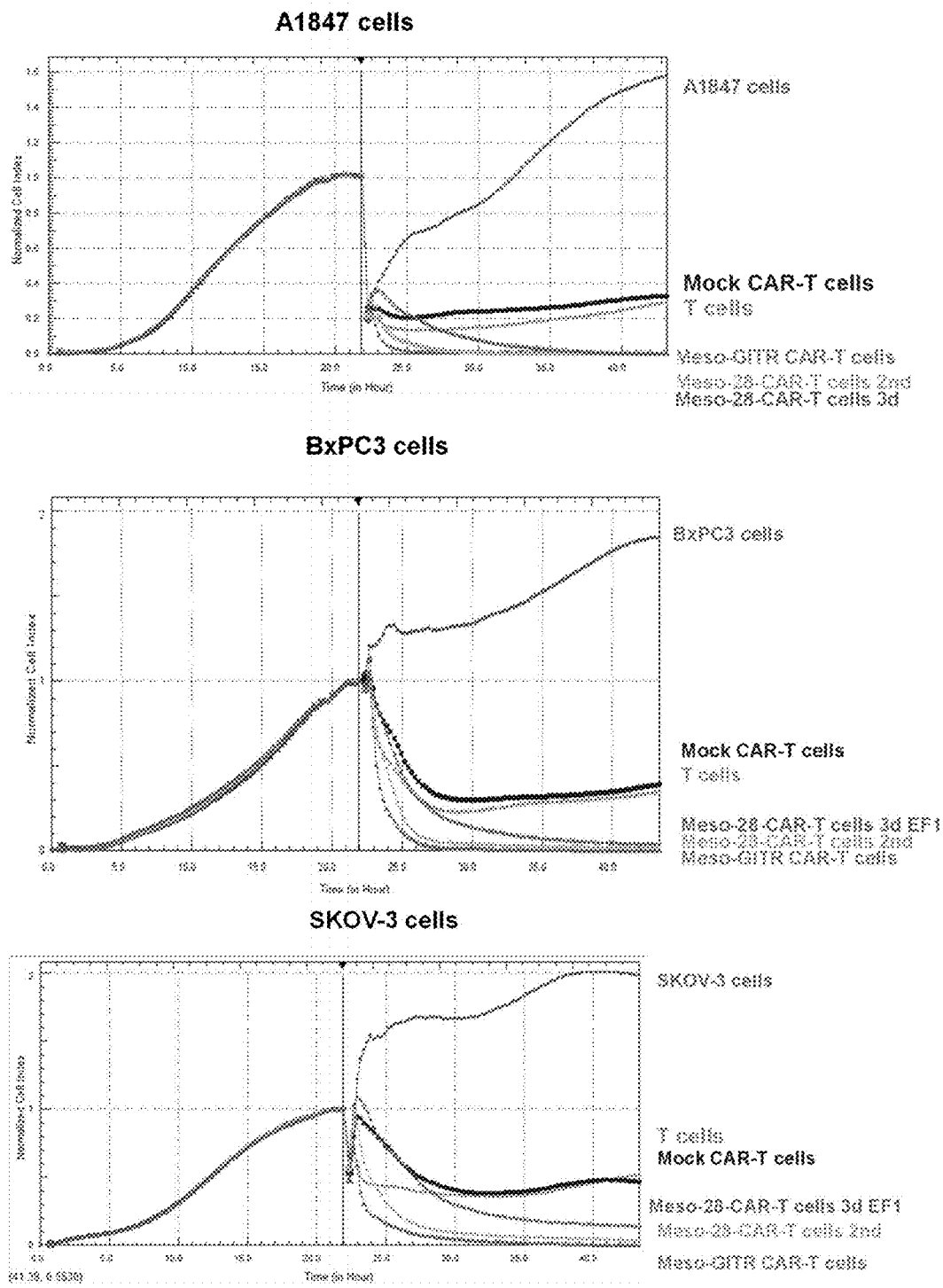
FIG. 7. Mesothelin-GITR-CD3 zeta CAR-T cells kill mesothelin-positive ovarian and pancreatic cancer cells.

Mesothelin-GITR-CD3 zeta CAR and mesothelin-CD28-CD3 zeta CAR killed mesothelin-positive cancer cells (FIG. 7) and had better activities than mesothelin-28-4-1BB-CD3 zeta (third generation) CAR-T cells. FIG. 7, bottom panel shows that in SKOV-3 cells, mesothelin-GITR-CAR-T cells killed faster than mesothelin-CD28-CD3 zeta CAR T cells and mesothelin-28-4-1BB-CD3 zeta CAR-T cells.

Figure 8:
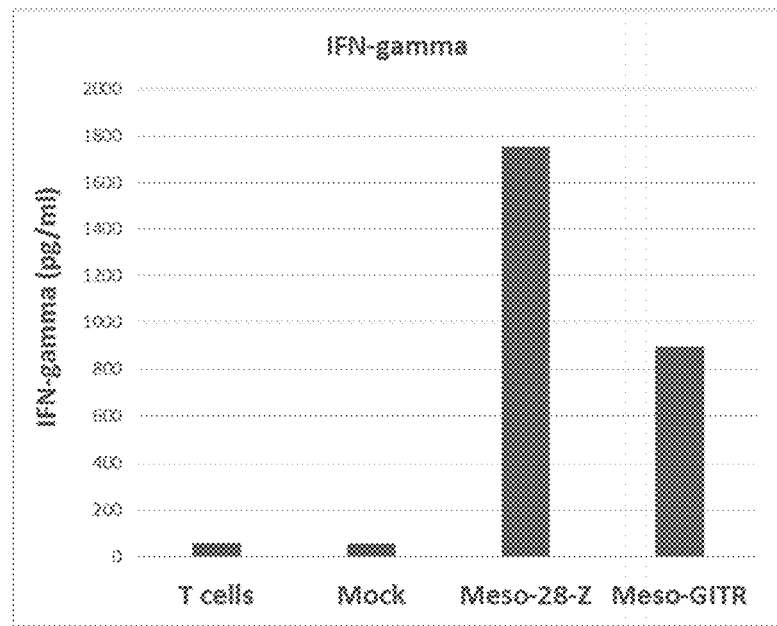
FIG. 8. Mesothelin-GITR CAR-T cells produce >2 fold less IFN-gamma cytokine than mesothelin-28-CD3 zeta in BxPC3 cells.

Example 18. Mesothelin-GITR CAR-T Cells had the Same Cytotoxic Activity Against Cancer Cells and Produced Less IFN-Gamma Cytokine than Mesothelin-CD28 CAR-T Cells We tested mesothelin-GITR-CD3 zeta CAR-T cells and mesothelin-CD28-CD3 zeta; both had about the same cytotoxic activity against BxPC3 cancer cells, for their production of cytokine IFN-gamma. Mesothelin-GITR-CD3 zeta CAR T cells secreted 2-fold less IFN-gamma than that secreted by mesothelin-CD28-CD3 zeta CAR T cells (FIG. 8), which suggests that mesothelin-GITR-CD3 zeta CAR-T cells may have advantages in clinic due to less cytokine release syndrome in patients.

Figure 9:
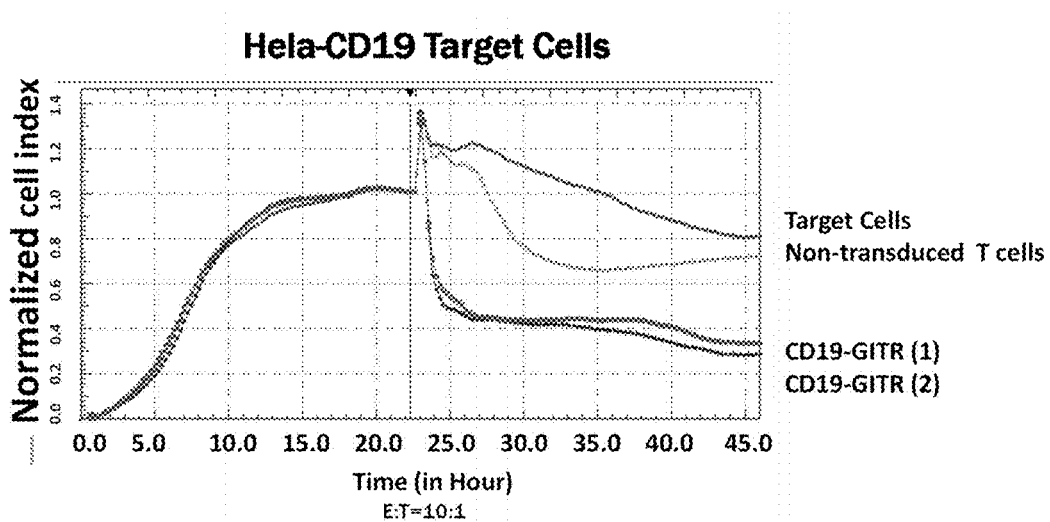
FIG. 9. CD19-GITR-CD3 zeta CAR-T cells kill CD19-positive Hela-CD19 cells. CAR-T to target cells ratio is 10:1. CD19-GITR-z denotes CD19-GITR-CD3 zeta. (1) and (2) show different CD19 constructs that differ in their TM domain. CD19-GITR-z (1) has CD8 transmembrane domain and CD19-GITR-z (2) has CD28 TM domain. Both constructs have about the same cytolytic activity against Cd19-positive cancer cells.

Example 19. CD19-GITR-CD3 Zeta CAR Expressed High Cytotoxic Activity Against CD19-Positive Cancer Cells We generated CD19-GITR-CD3 zeta with CD8 transmembrane domain and CD28 transmembrane domain CAR-T cells and compared their cytolytic activities against Hela-CD19+ positive cells. Both CD19-GITR CAR-T cells had >50% killing activity (FIG. 9). The CD19-CD28-CD3 zeta had 100% killing activity (not shown). The less activity of CD19-GITR CAR-T cells can result in less toxicity against normal cells in clinic and can have advantages in future clinical trials.

Figure 10:
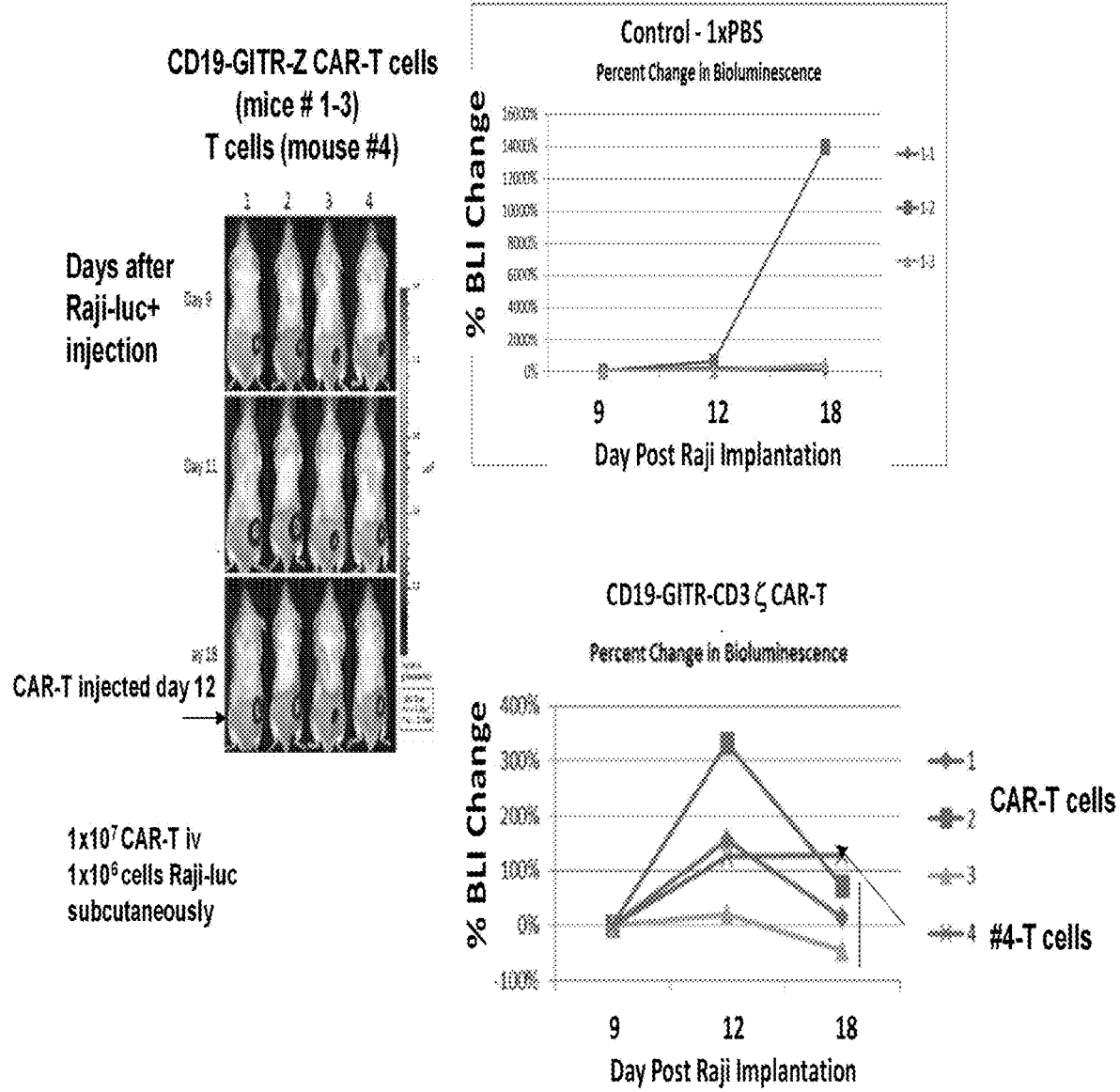
FIG. 10. CD19-GITR-CD3 zeta CAR-T cells decrease tumor growth in Raji-luciferase+ xenograft NSG mouse model. Three mice were treated with CAR-T cells, 3 mice with 1×PBS, and one mice with T cells.

Example 20. EGFR-GITR-CD3 Zeta CAR Blocked Tumor Growth of Raji Leukemia Cells in Mice We compared the in vivo killing activity of CD19-GITR-CD3 zeta CAR-T cells in Raji xenograft mouse model. Raji-luciferase+cells were subcutaneously injected into NSG mice. At day 12, CD19-GITR-CAR-T cells ($1\times10^7$ cells/mice) were injected intravenously when tumors reached >50 $mm^3$. CD19-GITR-CD3 zeta CAR-T cells decreased bioluminescent intensity (BLI) versus 1×PBS control-treated mice or mice with injected T cells control (FIG. 10). The results demonstrate high in vivo efficacy of CD19-GITR-CD3 zeta CAR-T cells. All three mice treated with Cd19-GITR-Cd3 CAR-T cells decreased BLI in contrast to control groups that had either increased or unchanged signals (FIG. 10).

REFERENCES

1. Maus, M. V., Haas, A. R., Beatty, G. L., Albelda, S. M., Levine, B. L., Liu, X., Zhao, Y., Kalos, M., and June, C. H. (2013). T cells expressing chimeric antigen receptors can cause anaphylaxis in humans. Cancer Immunol Res 1, 26-31.
2. Maus, M. V., Grupp, S. A., Porter, D. L., and June, C. H. (2014). Antibody-modified T cells: CARs take the front seat for hematologic malignancies. Blood 123, 2625-2635.
3. Lemmon, M. A., Schlessinger, J., and Ferguson, K. M. (2014). The EGFR family: not so prototypical receptor tyrosine kinases. Cold Spring Harb Perspect Biol 6, a020768.
4. Choi, B. D., Archer, G. E., Mitchell, D. A., Heimberger, A. B., McLendon, R. E., Bigner, D. D., and Sampson, J. H. (2009). EGFRvIII-targeted vaccination therapy of malignant glioma. Brain Pathol 19, 713-723.
5. Liu, X., Jiang, S., Fang, C., Yang, S., Olalere, D., Pequignot, E. C., Cogdill, A. P., Li, N., Ramones, M., Granda, B., et al. (2015). Affinity-Tuned ErbB2 or EGFR Chimeric Antigen Receptor T Cells Exhibit an Increased Therapeutic Index against Tumors in Mice. Cancer Res 75, 3596-3607.
6. Maus, M. V., and June, C. H. (2014). CARTs on the road for myeloma. Clin Cancer Res 20, 3899-3901.
7. Morello, A., Sadelain, M., and Adusumilli, P. S. (2016). Mesothelin-Targeted CARs: Driving T Cells to Solid Tumors. Cancer Discov 6, 133-146.
8. Lamers, C. H., Willemsen, R., van Elzakker, P., van Steenbergen-Langeveld, S., Broertjes, M., Oosterwijk-Wakka, J., Oosterwijk, E., Sleijfer, S., Debets, R., and Gratama, J. W. (2011). Immune responses to transgene and retroviral vector in patients treated with ex vivo-engineered T cells. Blood 117, 72-82.
9. Beatty, G. L., Haas, A. R., Maus, M. V., Torigian, D. A., Soulen, M. C., Plesa, G., Chew, A., Zhao, Y., Levine, B. L., Albelda, S. M., et al. (2014). Mesothelin-specific chimeric antigen receptor mRNA-engineered T cells induce anti-tumor activity in solid malignancies. Cancer Immunol Res 2, 112-120.
10. Lanitis, E., Poussin, M., Hagemann, I. S., Coukos, G., Sandaltzopoulos, R., Scholler, N., and Powell, D. J., Jr. (2012). Redirected antitumor activity of primary human lymphocytes transduced with a fully human anti-mesothelin chimeric receptor. Mol Ther 20, 633-643.
11. Maus, M. V., and June, C. H. (2013). Zoom Zoom: racing CARs for multiple myeloma. Clin Cancer Res 19, 1917-1919.
12. Kochenderfer, J. N., and Rosenberg, S. A. (2013). Treating B-cell cancer with T cells expressing anti-CD19 chimeric antigen receptors. Nat Rev Clin Oncol 10, 267-276.
13. Kochenderfer, J. N., Feldman, S. A., Zhao, Y., Xu, H., Black, M. A., Morgan, R. A., Wilson, W. H., and Rosenberg, S. A. (2009). Construction and preclinical evaluation of an anti-CD19 chimeric antigen receptor. J Immunother 32, 689-702.
14. Ramos, C. A., Savoldo, B., and Dotti, G. (2014). CD19-CAR trials. Cancer J 20, 112-118.
15. Knee, D. A., Hewes, B., and Brogdon, J. L. (2016). Rationale for anti-GITR cancer immunotherapy. Eur J Cancer 67, 1-10.
16. Zhou, Y., Drummond, D. C., Zou, H., Hayes, M. E., Adams, G. P., Kirpotin, D. B., and Marks, J. D. (2007). Impact of single-chain Fv antibody fragment affinity on nanoparticle targeting of epidermal growth factor receptor-expressing tumor cells. J Mol Biol 371, 934-947.
17. Lanitis, E., et al. (2012) Redirected antitumor activity of primary human lymphocytes transduced with a fully human anti-mesothelin chimeric receptor. Mol Ther 20, 3, 633-643.
18. Kochenderfer J N, et al. (2009) Construction and preclinical evaluation of an anti-CD19 chimeric antigen receptor. J Immunother 82/7 689-702

What is claimed is:

1. A chimeric antigen receptor fusion protein comprising the amino acid sequence of SEQ ID NO: 2, 25, or 27, or at least 95% sequence identity thereof.

2. A chimeric antigen receptor fusion protein comprising from N-terminus to C-terminus:
   (i) a single-chain variable fragment (scFv) that binds to a human epidermal growth factor receptor (EGFR), wherein the scFv comprising VH having the amino acid sequence of SEQ ID NO: 16 and VL having the amino acid sequence of SEQ ID NO: 18,
   (ii) a transmembrane domain,
   (iii) a co-stimulatory domain of a glucocorticoid-induced TNFR-related protein (GITR) intracellular domain comprising the amino acid sequence of SEQ ID NO: 12, and
   (iv) an activating domain.

3. The fusion protein according to claim 2, wherein the transmembrane domain is human CD28 or human CD8.

4. The fusion protein according to claim 2, wherein the activating domain is CD3 zeta.

5. The chimeric antigen receptor fusion protein of claim 2, wherein the scFv has the amino acid sequence of SEQ ID NO: 6.

6. The fusion protein according to claim 5, wherein the transmembrane domain is human CD28 or human CD8.

7. The fusion protein according to claim 5, wherein the activating domain is CD3 zeta.

* * * * *